(12) United States Patent
McChesney et al.

(10) Patent No.: US 8,801,924 B2
(45) Date of Patent: Aug. 12, 2014

(54) CHROMATOGRAPHY METHODS

(75) Inventors: James D. McChesney, Etta, MS (US); Douglas L. Rodenburg, Thaxton, MS (US)

(73) Assignee: IronStone Separations, Inc., Etta, MS (US)

( * ) Notice: Subject to any disclaimer, the term of this patent is extended or adjusted under 35 U.S.C. 154(b) by 0 days.

(21) Appl. No.: 13/807,255

(22) PCT Filed: Jul. 7, 2011

(86) PCT No.: PCT/US2011/043233
§ 371 (c)(1),
(2), (4) Date: Feb. 6, 2013

(87) PCT Pub. No.: WO2012/030432
PCT Pub. Date: Mar. 8, 2012

(65) Prior Publication Data
US 2013/0199999 A1 Aug. 8, 2013

Related U.S. Application Data

(60) Provisional application No. 61/362,169, filed on Jul. 7, 2010.

(51) Int. Cl.
*B01D 15/08* (2006.01)

(52) U.S. Cl.
USPC .......................... 210/198.2; 210/656

(58) Field of Classification Search
USPC .............. 210/635, 656, 659, 198.2, 232, 238; 141/12, 73, 80; 95/82; 96/101
See application file for complete search history.

(56) References Cited

U.S. PATENT DOCUMENTS

| | | | | |
|---|---|---|---|---|
| 4,361,482 A | * | 11/1982 | Teetz et al. | 210/198.2 |
| 5,674,455 A | * | 10/1997 | Marchand et al. | 422/70 |
| 5,951,873 A | * | 9/1999 | Shalon et al. | 210/656 |
| 6,036,855 A | * | 3/2000 | Shalon et al. | 210/198.2 |
| 2004/0241866 A1 | * | 12/2004 | Collins et al. | 436/55 |
| 2006/0027502 A1 | * | 2/2006 | Gill et al. | 210/656 |
| 2010/0163490 A1 | * | 7/2010 | Lasalle | 210/656 |

* cited by examiner

*Primary Examiner* — Ernest G Therkorn
(74) *Attorney, Agent, or Firm* — Sam L. Nguyen; Hamilton, DeSanctis & Cha, LLP

(57) ABSTRACT

This application discloses, in part, 1) a stationary phase column and compression designs for preparative chromatography, 2) a method of improving performance of silica gel chromatography by controlling the hydration of silica gel and acidifying the mobile phase, and 3) a method of extending the life of a silica gel column packing by cleaning or regenerating the silica gel stationary phase.

6 Claims, 12 Drawing Sheets

| solvent system | replicate | Paclitaxel RT | width | symmetry | Baccatin III RT | width | symmetry | 10 DAB III RT | width | symmetry | |
|---|---|---|---|---|---|---|---|---|---|---|---|
| dry | 1 | 5.275 | 0.163 | 0.332 | 6.067 | 0.164 | 0.333 | 14.486 | 0.702 | 0.132 | |
|  | 2 | 5.476 | 0.212 | 0.287 | 6.279 | 0.227 | 0.251 | 14.690 | 0.788 | 0.122 | |
|  | 3 | 5.487 | 0.213 | 0.284 | 6.286 | 0.229 | 0.250 | 14.700 | 0.790 | 0.123 | |
|  | 4 | 5.489 | 0.214 | 0.286 | 6.288 | 0.228 | 0.249 | 14.706 | 0.797 | 0.121 | |
|  | 5 | 5.490 | 0.214 | 0.288 | 6.292 | 0.227 | 0.250 | 14.712 | 0.798 | 0.122 | |
| acidified | 1 | 5.209 | 0.179 | 0.332 | 5.943 | 0.189 | 0.314 | 11.907 | 0.420 | 0.242 | |
|  | 2 | 5.111 | 0.162 | 0.392 | 5.934 | 0.171 | 0.353 | 13.390 | 0.574 | 0.152 | |
|  | 3 | 5.108 | 0.160 | 0.391 | 5.930 | 0.171 | 0.355 | 13.382 | 0.562 | 0.155 | |
|  | 4 | 5.098 | 0.159 | 0.394 | 5.918 | 0.172 | 0.358 | 13.346 | 0.543 | 0.154 | |
|  | 5 | 5.096 | 0.159 | 0.399 | 5.914 | 0.172 | 0.361 | 13.318 | 0.531 | 0.152 | |
| dry | 1 | 5.249 | 0.169 | 0.372 | 6.120 | 0.184 | 0.326 | 14.391 | 0.614 | 0.148 | |
|  | 2 | 5.480 | 0.211 | 0.293 | 6.290 | 0.221 | 0.262 | 14.749 | 0.792 | 0.122 | |
|  | 3 | 5.480 | 0.210 | 0.293 | 6.292 | 0.222 | 0.259 | 14.748 | 0.783 | 0.122 | |
|  | 4 | 5.480 | 0.211 | 0.297 | 6.294 | 0.220 | 0.263 | 14.746 | 0.782 | 0.122 | |
|  | 5 | 5.471 | 0.209 | 0.295 | 6.286 | 0.220 | 0.264 | 14.715 | 0.785 | 0.122 | |
| wet | 1 | 5.234 | 0.200 | 0.322 | 6.082 | 0.192 | 0.298 | 12.271 | 0.295 | 0.617 | |
|  | 2 | 5.253 | 0.147 | 0.904 | 5.894 | 0.154 | 0.893 | 12.358 | 0.321 | 0.868 | |
|  | 3 | 5.150 | 0.166 | 1.054 | 5.749 | 0.175 | 1.076 | 12.085 | 0.366 | 1.062 | |
|  | 4 | 5.049 | 0.212 | 1.359 | 5.622 | 0.226 | 1.417 | 11.843 | 0.407 | 1.421 | reintegrated |
|  | 5 | 4.937 | 0.240 | 1.447 | 5.492 | 0.360 | 1.589 | 11.584 | 0.531 | 1.599 | reintegrated |
| dry | 1 | 4.800 | 0.200 | 0.843 | 5.330 | 0.207 | 0.841 | 11.249 | 0.461 | 0.764 | |
|  | 2 | 5.412 | 0.153 | 0.717 | 6.076 | 0.173 | 0.668 |  | double peak |  | |
|  | 3 | 5.444 | 0.200 | 0.327 | 6.291 | 0.207 | 0.280 | 14.868 | 0.738 | 0.129 | |
|  | 4 | 5.455 | 0.201 | 0.318 | 6.297 | 0.211 | 0.276 | 14.874 | 0.744 | 0.128 | |
|  | 5 | 5.465 | 0.205 | 0.314 | 6.301 | 0.214 | 0.270 | 14.881 | 0.761 | 0.125 | |
| wa | 1 | 3.874 | 0.045 | 0.718 | 4.846 | 0.216 | 0.434 | 10.637 | 0.272 | 0.702 | Peak IDs not clear |
|  | 2 | 4.853 | 0.126 | 0.870 | 5.442 | 0.130 | 0.847 | 10.867 | 0.251 | 0.815 | |
|  | 3 | 4.729 | 0.123 | 0.880 | 5.280 | 0.125 | 0.859 | 10.568 | 0.242 | 0.830 | |
|  | 4 | 4.638 | 0.122 | 0.877 | 5.167 | 0.126 | 0.875 | 10.351 | 0.237 | 0.846 | |
|  | 5 | 4.546 | 0.119 | 0.883 | 5.057 | 0.123 | 0.881 | 10.125 | 0.233 | 0.860 | |
| wa + regen | 1 | 4.464 | 0.116 | 0.900 | 4.945 | 0.120 | 0.904 | 10.033 | 0.228 | 0.885 | |

Figure 2. Table of Taxane Raw date

| solvent | # | Paclitaxel | | | Baccatin III | | | 10 DAB III | | | |
|---|---|---|---|---|---|---|---|---|---|---|---|
| 5% water | 2 | 4.314 | 0.159 | 1.358 | 4.784 | 0.157 | 1.492 | 9.776 | 0.327 | 1.714 | |
| 5% methanol | 3 | 4.178 | 0.157 | 1.374 | 4.626 | 0.153 | 1.529 | 9.482 | 0.327 | 1.820 | |
| 1% HOAc | 4 | 4.058 | 0.158 | 1.354 | 4.488 | 0.156 | 1.488 | 9.211 | 0.331 | 1.773 | |
| 1 CV | 5 | 3.925 | 0.161 | 1.456 | 4.346 | 0.154 | 1.469 | 8.940 | 0.328 | 1.723 | |
|  | 6 | 3.810 | 0.152 | 1.275 | 4.219 | 0.152 | 1.485 | 8.678 | 0.316 | 1.680 | |
| wa + regen | 1 | 3.747 | 0.148 | 1.270 | 4.151 | 0.151 | 1.455 | 8.590 | 0.313 | 1.523 | |
| dry | 2 | 4.342 | 0.160 | 1.296 | 4.822 | 0.165 | 1.365 | 9.997 | 0.343 | 1.446 | |
| EtOAc | 3 | 4.831 | 0.131 | 0.893 | 5.449 | 0.142 | 0.912 | 11.267 | 0.283 | 0.833 | |
| 2 CV regen | 4 | 5.026 | 0.128 | 0.872 | 5.710 | 0.131 | 0.837 | 11.683 | 0.269 | 0.781 | |
| 2 cv equil | 5 | 5.030 | 0.128 | 0.871 | 5.715 | 0.131 | 0.836 | 11.689 | 0.267 | 0.784 | |
|  | 6 | 5.027 | 0.128 | 0.874 | 5.713 | 0.131 | 0.834 | 11.689 | 0.266 | 0.783 | |
|  | 7 | 5.030 | 0.128 | 0.871 | 5.716 | 0.131 | 0.837 | 11.692 | 0.266 | 0.779 | |
|  | 8 | 5.029 | 0.129 | 0.869 | 5.716 | 0.131 | 0.837 | 11.694 | 0.266 | 0.780 | |
|  | 9 | 5.030 | 0.129 | 0.871 | 5.717 | 0.133 | 0.834 | 11.695 | 0.266 | 0.777 | |
|  | 10 | 5.032 | 0.129 | 0.873 | 5.718 | 0.131 | 0.831 | 11.696 | 0.266 | 0.780 | |
|  | 11 | 5.030 | 0.129 | 0.870 | 5.717 | 0.133 | 0.834 | 11.696 | 0.266 | 0.781 | |
|  | 12 | 5.029 | 0.129 | 0.869 | 5.717 | 0.133 | 0.834 | 11.695 | 0.266 | 0.777 | |
|  | 13 | 5.030 | 0.129 | 0.870 | 5.717 | 0.133 | 0.834 | 11.695 | 0.267 | 0.780 | |
|  | 14 | 5.030 | 0.129 | 0.869 | 5.717 | 0.133 | 0.834 | 11.695 | 0.266 | 0.778 | |
| wa + regen | 1 | 4.997 | 0.127 | 0.884 | 5.638 | 0.129 | 0.851 | 11.472 | 0.259 | 0.804 | new batch MP |
| 5% MeOH | 2 | 4.970 | 0.127 | 0.866 | 5.652 | 0.131 | 0.831 | 11.518 | 0.263 | 0.778 | |
| EtOAc | 3 | 4.975 | 0.127 | 0.866 | 5.658 | 0.131 | 0.833 | 11.529 | 0.263 | 0.771 | |
| dry 2cv | 4 | 4.976 | 0.128 | 0.865 | 5.659 | 0.132 | 0.831 | 11.532 | 0.263 | 0.772 | |
| regen 2cv equil | 5 | 4.977 | 0.128 | 0.867 | 5.660 | 0.131 | 0.830 | 11.534 | 0.263 | 0.778 | |
|  | 6 | 4.976 | 0.128 | 0.865 | 5.660 | 0.131 | 0.830 | 11.534 | 0.263 | 0.774 | |
|  | 7 | 4.979 | 0.128 | 0.871 | 5.663 | 0.131 | 0.835 | 11.536 | 0.263 | 0.779 | |
|  | 8 | 4.978 | 0.128 | 0.868 | 5.662 | 0.131 | 0.833 | 11.535 | 0.263 | 0.777 | |
|  | 9 | 4.977 | 0.128 | 0.866 | 5.661 | 0.131 | 0.831 | 11.534 | 0.264 | 0.771 | |
|  | 10 | 4.980 | 0.127 | 0.867 | 5.664 | 0.131 | 0.828 | 11.538 | 0.263 | 0.772 | |

Figure 2 (continued). Table of Taxane Raw data

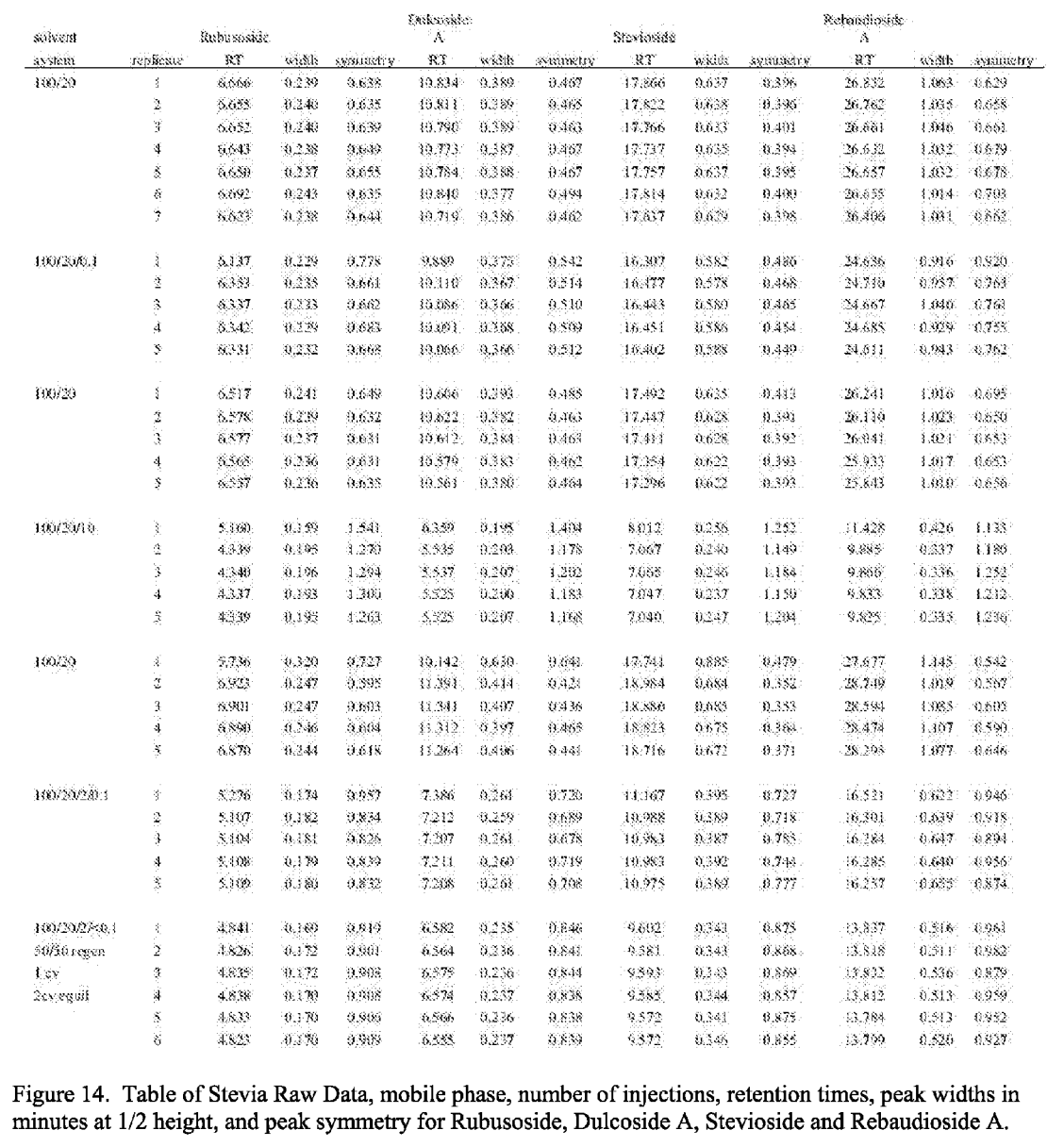

Figure 14. Table of Stevia Raw Data, mobile phase, number of injections, retention times, peak widths in minutes at 1/2 height, and peak symmetry for Rubusoside, Dulcoside A, Stevioside and Rebaudioside A.

| Solvent system | replicate | Lutein RT | symmetry | Zeaxanthin RT | symmetry |
|---|---|---|---|---|---|
| wet | 1 | 3.932 | 0.892 | 4.231 | 0.899 |
|  | 2 | 3.997 | 0.893 | 4.312 | 0.887 |
|  | 3 | 4.104 | 0.902 | 4.437 | 0.891 |
|  | 4 | 4.150 | 0.904 | 4.496 | 0.892 |
|  | 5 | 4.149 | 0.905 | 4.494 | 0.890 |
| dry | 1 | 4.000 | 0.905 | 4.309 | 0.890 |
|  | 2 | 4.723 | 0.909 | 5.240 | 0.940 |
|  | 3 | 4.731 | 0.906 | 5.248 | 0.946 |
|  | 4 | 4.716 | 0.905 | 5.229 | 0.944 |
|  | 5 | 4.714 | 0.909 | 5.226 | 0.935 |
|  | 6 | 4.721 | 0.907 | 5.231 | 0.903 |
| wet | 1 | 4.466 | 0.900 | 4.913 | 0.818 |
|  | 2 | 4.174 | 0.902 | 4.519 | 0.844 |
|  | 3 | 4.171 | 0.901 | 4.516 | 0.840 |
|  | 4 | 4.180 | 0.903 | 4.526 | 0.829 |
Figure 23. Table of Carotenoid Raw Data, mobile phase, number of injections, retention times and peak symmetry for Lutein and Zeaxanthin.
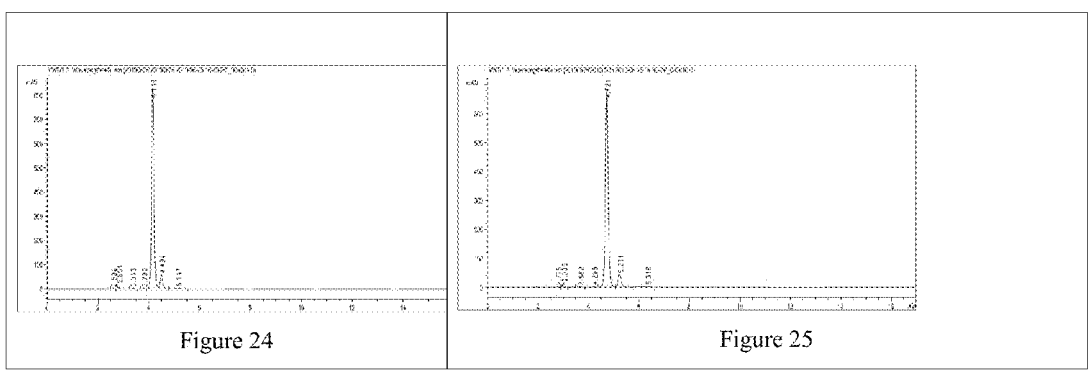
Figure 24 | Figure 25

CHROMATOGRAPHY METHODS

PRIORITY APPLICATIONS

The present application claims priority under 371 to International Patent Application No. PCT/US11/43233, filed Jul. 7, 2011, which claims priority to U.S. Provisional Patent Application Ser. No. 61/362,169, filed Jul. 7, 2010, which are incorporated herein by reference in their entirety.

TECHNICAL FIELD

One embodiment of the application relates to an apparatus and methods for liquid chromatography, particularly to a preparative chromatography column apparatus and methods to improve normal phase column performance and longevity of the normal phase stationary phase.

BACKGROUND OF THE INVENTION

The separation and purification of principals from complex mixtures routinely employs preparative column chromatography. Column chromatography is a separation technology wherein the mixture to be separated is passed through a column of an adsorbent (the stationary phase) as a solution in a solvent mixture (the mobile phase). A column stationary phase (media) is packed into a bed and is generally porous and has a large surface area through which the liquid mobile phase is pumped. The various compounds of the mixture partition between the stationary phase and the mobile phase according to their relative affinity to the two phases (their partition co-efficient). Since the partition co-efficient is a property unique to the specific chemical structure of each compound in the mixture, the compounds will differentially partition between the phases such that those having higher affinity to the mobile phase will be washed through the column most quickly and those having highest affinity for the stationary phase will be retained in the column longest. This differential of rates of passage through the column thereby accomplishes the desired separation. Complex mixtures of compounds can often be separated with chromatography into single compound pools in a single step procedure. Columns used in chromatography comprise a tubular body enclosing the porous stationary phase through which the mobile phase is pumped with separation effected by the portioning of the components of the mixture to be separated between the mobile and stationary phases. Prior to any separation by chromatography, the packed bed of stationary phase must be prepared starting with a suspension of particles or slurry that has to be introduced into the column. The process of bed formation is called "the packing procedure" and a well packed bed is critical to adequate performance of the separations performed with the chromatographic column. The slurry is uniformly and rapidly compacted into the column under pressure forming the packed bed. The packed bed is maintained under high pressure and density to achieve the most efficient separation of the mixture being chromatographed. The goal of the packing procedure is to provide a bed compressed by the optimum amount of compression.

The porous stationary phase is formed by consolidation of a slurry of discrete particles that is pumped, poured or sucked into the column. Consolidation of the slurry into a packed bed is typically accomplished by filtering it against a particle retaining filter and further compressing the formed filter cake so that it is packed into a volume which is less than the volume that it would have occupied if it had sedimented under the influence of gravity to form a sedimented bed. The efficiency of subsequent chromatographic separations is influenced by the liquid distribution and collection system at the fluid inlet and outlet of the packed bed, but most importantly by the homogeneity of the packed bed formed during packing and its continued stability. If the packed bed is not homogeneous and stable, subsequent chromatographic separations performed with the chromatographic column will be deleteriously effected. Homogeneity and stability of the packed bed depend on the optimum degree of compression which must be determined experimentally for each column diameter, bed height, and bed medium. Several methods are known in the art for packing columns Flow Packing is a method usually used for packing analytical columns (columns of 1 to 10 mm in diameter) and semi-preparative columns (columns of 10 to 100 mm in diameter). In Flow Packing one end of the column is closed by a frit or a filter. The pores of the frit are sized to permit the liquid of the slurry to flow out of the column while preventing discharge of the packing material. At the other end, a slurry of the stationary phase is pumped or poured into the column. A filtration bed builds up against the exit frit and grows until a filter cake is formed. The bed is then compressed further to its target bed height by percolating a number of column volumes (usually more than 5) of a packing solvent at a flow rate that is higher than the flow rates used in operation. Consolidation and subsequent compression take place under the influence of the seepage force, that is the reaction of the bed to the pressure gradient required to maintain flow rate of the packing solvent through the packed bed. Once the bed is compressed by the flow, the solvent flow is stopped, the outlet of the column sealed and an upper end (inlet) cell is adjusted to the target height of the compressed bed. This adjustment is done quickly to avoid a relaxation of the compressed bed exceeding the target bed height. The flow packing method has the disadvantage that beds of packing material compressed in this manner are axially heterogeneous during the flow compression step yielding highest compression close to the column outlet and zero compression at the top of the packed bed. This results in a major relaxation of the bed and a possible re-arrangement of the particles once the packing flow has been stopped and the inlet end has been brought into place. The gradient in bed compression inherent to this method of packing may result in poor bed stability and poor column efficiency depending on the type of medium and the packed bed geometry. This is especially likely in the case of large scale preparative columns.

Flow Packing methods may not be suitable for wide bore columns used in preparative chromatography. Among other factors, it is not desirable to design and fabricate equipment that requires application of a packing flow rate and thus a packing pressure substantially higher than the pressure required for subsequent operation of the large scale of preparative chromatography. To overcome this problem, packing methods which employ mechanical axial compression are used. Axial compression methods achieve the bed compression by an axial movement of a piston slidable within the column, an inlet opening through the piston covered by an inlet frit with pores sized to allow solvent flow but not exit of the packing medium. The need for high liquid pressure in the column body is avoided. A further advantage of the axial compression method is that the bed is compressed homogeneously in an axial direction which avoids the problems of relaxation and particle re-arrangements that occur with the Flow Packing method. Conventionally, when the chromatographic medium within the column is packed, a telescoping rod of a pushing device pushes the piston into the column. This compression packs the packing material to a predetermined pressure. It is the gradient of compression and bed voidage in axial direction that is substantially different between the Flow Packing and the axial compression method.

A disadvantage of axial compression is that columns packed using this method require a means for moving the piston and a means for controlling this movement. Typical methods for the movement are motor drives or hydraulic systems. As these are attached to or built into the column, the cost and mechanical complexity of axial compression columns is substantially greater than for Flow Packing columns. In addition, with the conventional axial compression method of packing chromatographic columns, the pushing device maintains the compression pressure on the packed bed via the piston. This requires that the pushing device remain attached to the column during operation of the chromatographic separation, further complicating the operation of the chromatographic system, especially at preparative scale.

Two contrasting approaches are routinely taken to affect chromatographic separations: 1) the mobile phase is less polar (more organic) than the stationary phase; so called "normal" phase chromatography, and 2) the mobile phase is more polar (aqueous) than the stationary phase; so called "reverse" phase chromatography. Reverse phase chromatography is perceived to have economic advantages over normal phase chromatography due to the usual practice of replacement of the normal phase adsorbent after one or at most a few uses whereas the reverse phase adsorbent can be used for hundreds of separations. The gravitation to reverse phase technology for preparative separations has occurred even in spite of the recognized advantages of normal phase chromatography due to significantly greater capacity per column run and ease of compound recovery from the organic solvent of the mobile phase, both very important advantages for production scale separations. At production scale, the energy required to recycle the normal phase organic solvents is less than that of reversed phase aqueous solvents. The waste disposal costs are reduced for the normal phase organic solvents because of their usually higher BTU content.

Because of the perception that normal phase adsorbents are not reusable or of a very limited useful life, less expensive poor quality normal phase adsorbents are typically employed in preparative column packings. The poorer quality normal phase adsorbent is usually of irregular shaped particles and possesses a wide particle size distribution which together give poor chromatographic performance for the packed bed. High quality normal phase adsorbents are available with spherical particles and narrow particle size distributions. As quality normal phase adsorbent costs about $5,000 per kilogram and is perceived not to be reusable, development of normal phase chromatographic processes has largely been avoided or not considered. With the technologies provided by the present application normal phase chromatographic processes can be developed providing cost savings to users through better performance, higher capacity, easier product recovery, less costly solvent recovery, and less costly solvent disposal.

DESCRIPTION OF PRIOR ART

U.S. Pat. Nos. 5,951,873 and 6,036,855 teach that helical springs can be employed for dynamic axial bed compression. The disadvantage to helical springs is that they are not capable of providing the large forces needed for the higher pressures required for adequate solvent flow when using smaller stationary phase particle sizes.

No prior art for internally threaded preparative column has been found. Preparative or production sized chromatography columns are constructed using flanged inlet and/or outlet connections. The disadvantages of flanged connections are that at larger forces these flanges become increasingly thick and heavy. For example, a 600 lb class 316 SS blind flange for a 3" pipe rated for 1440 psi weighs 20 pounds, is 8.25 inches in diameter, and 1.25 inches thick. Its mating flange which is welded to the tube weighs 18 pounds. Assembly of these two flanges to seal one end of this column requires 8 each 3 inch×¾ inch bolts, for a total weight of about 40 pounds for one column end. Production scale columns designed this way are much heavier and larger than they need to be.

No prior art for control of silica gel hydration has been found. In the art, normal phase columns are prepared with inexpensive silica gels and are discarded after a single use, or at most a few uses. This is because there has been no way to restore performance after it degrades. No prior art for acidifying normal phase mobile phases has been found. No prior art for regeneration of normal phase adsorbents has been found.

SUMMARY OF THE INVENTION

One embodiment of the present application provides a preparative column design which provides automatic high pressure continuous dynamic axial compression of the chromatography bed without the prior art drawbacks of external mechanical or hydraulic equipment and periodic re-compression.

Disc spring washers and Belleville spring washers are different descriptors for the same thing. The disc spring washers supply the forces necessary for dynamic compression of the bed at the higher solvent pressures used for smaller particle sized stationary phases. A piston with a solvent distribution and sealing assembly is inserted into the column followed by an appropriate set of disc springs. The disc springs are compressed and held in place by a nut which is threaded into the end of the column. Disc springs provide a great deal of flexibility. They can be stacked in parallel summing the springs' forces giving a large range of total forces that can be available. Single disc springs in parallel stacks can be stacked in series summing the stacks' deflection to provide variable total deflection. Selection of a particular disc spring and stacking it in a series of parallel stacks allows the column design to accommodate a range of pressure on the chromatography bed with a range of distance over which the compressive force will be applied. The chromatography bed is initially compressed by a combination of flow packing and axial compression during the packing and assembly process. The chromatographic bed may relax or settle during use. As it does the disc springs take up the slack while continuing to apply axial compression.

Another aspect of the application is to provide a preparative chromatography column design which overcomes the drawback of the prior art of heavy flanged chromatography column. An internally threaded inlet and/or outlet design significantly reduces the weight and size of an assembled preparative chromatography column. This is accomplished by increasing the wall thickness to accommodate the threads. The weight and size of an assembled column is significantly reduced with this design. A nominal 7.5 cm internal diameter column by 50 cm bed length weighs approximately 50 lbs and has on outer diameter of approximately 3.75 inches compared to a flanged design of the same internal dimensions and pressure rating which weighs approximately 100 lbs and has an outer flange diameter of 8.25 inches.

Another aspect of the application is to provide a method of normal phase chromatography operation which overcomes the drawback of the prior art methods.

A column packed with silica gel stationary phase and run with technical or better grades of organic solvents will show increasing peak broadening as it is used for more and more column runs. It has been discovered that this is due to two reasons.

The first relates to the hydration of the silica gel. Newly packed silica gel is hydrated to some uncontrolled extent of about 5% by weight for normal packaging. The technical or better grades of organic solvent used in the operation of the normal phase chromatographic separation, usually as mixtures, contain a low concentration of water about 0.1% which is below saturation. These organic solvent mixtures have a capacity to hold water at a low concentration which is greater than the concentration of water typically present in fresh solvent. This concentration will vary depending on the specific solvent(s) or mixtures used. As the "dry" solvent flows over the hydrated silica gel stationary phase it absorbs water from the silica evidenced by the increased concentration of water in the mobile phase exiting the column compared to the concentration of water in the mobile phase entering the column. The mobile phase is drying the silica gel. The band width of the compounds in the mixture to be separated increases and the separation capability or performance of the column decreases as the silica is dried. This problem is overcome by the addition of water to near saturation of the mobile phase. When the silica gel and mobile phase are near an equilibrium for the concentrations of water the concentration of water in the mobile phase entering the column will be nearly the same as the concentration of water in the mobile phase exiting the column. With this water equilibrium established, the compound band width is reduced and the separation capability or performance of the column is improved, maintained or restored.

It also has been discovered that the addition of a small amount of organic acid such as acetic acid, 0.1 to 1% v/v, to the mobile phase has the benefit of further reducing the compound band width improving the separation capability or performance of the column.

Another object of the present application is to provide a method for cleaning of normal phase chromatography columns which overcomes the drawback of the prior art methods.

The second reason for decreased performance of normal phase chromatographic columns with multiple uses is that the mixtures of compounds to be separated frequently contain compounds that are highly retained by the silica. As additional column runs are performed, these highly retained compounds load up on the column and reduce its capacity to separate the mixtures adequately and may even slowly elute from the column contaminating later column runs. Guard columns which have capacity to retain highly bound impurities can be employed to reduce this problem, however the column will load up anyway at a reduced rate. The resolution to this problem of the column loading up is the use of a regeneration solvent after each column run or series of column runs. This regeneration solvent is of an appropriately increased polarity and will wash these highly retained compounds off the column thus restoring the capacity and performance of the column. Measurement of the mass of these compounds flushed off the column confirms this.

For example, a separation is performed using a typical normal phase solvent, ethyl acetate. The ethyl acetate becomes saturated with water at about 3%. Water is added to the ethyl acetate to 2% and 0.1% acetic acid is added. The mixture is mixed and allowed to absorb the water and equilibrate. The preparative separation is performed using this mobile phase. After the last of the compounds of interest have exited the column, a column volume of regeneration solvent comprised for example of 75% ethyl acetate, 20% methanol, 4% water and 1% acetic acid is introduced to the column followed by an equilibration volume, approximately 2 column volumes, of the original "wet acidified" (wa) ethyl acetate. As the regeneration solvent exits the column the highly retained compounds are flushed from the column. With respect to the water or hydration equilibrium, the initial regeneration solvent exiting the column will have lower concentrations of water in it, evidence that the silica gel stationary phase is adsorbing water. As the displacement of the regeneration solvent by the wet acidified ethyl acetate progresses, the concentration of methanol decreases to zero and the water concentration decreases as well. When the methanol concentration is zero, the ethyl acetate is saturated with water which is above the starting concentration of water in the mobile phase, evidence that the mobile phase is adsorbing water from the silica gel which was retained from the regeneration solution. As flow continues, the concentration of water in the mobile phase exiting the column will decrease and approach the concentration of water in the mobile phase entering the column. The column is now ready for the next separation.

In practice, the column does not need to be fully equilibrated before the next column run can be started. The performance of the subsequent separation does not appear to be particularly sensitive to incomplete re-equilibration and during the column run the mobile phase will continue to equilibrate the column. The degree necessary to which equilibrium is approached will vary for the specific separation and the solvent system that is employed. This can be optimized to minimize the volume of regeneration solvent used and the equilibration with mobile phase volume when performing repetitive column runs of similar mixture and mobile phase compositions.

With this technology, normal phase silica gel columns can be used for hundreds of column runs without re-packing and their separation capability is maintained effectively equivalent to the originally packed column, much above what heretofore has been expected for normal phase columns.

Embodiments and Aspects of the Invention:

In one embodiment, there is provided a method for improving a separation variable in a normal phase column chromatographic separation method for the separation of a composition comprising a mixture of components, wherein the method comprises increasing the water content in a mobile phase that is used as an eluting solvent in the normal phase column chromatographic separation method. In one aspect, the separation variable comprises the peak shape, resolution, column performance and/or efficiency of separation of the components. In one aspect, the improved separation properties provide the separation of at least one component of the mixture of components in a greater than 10%, 20%, 30%, 50%, 85% or 90% yield and at a higher purity. In another aspect, the method provides the at least one component with a 10%, 20%, 30%, 40% or 50% higher purity than the column chromatographic separation method in the absence of the control or increase of the water content. In one aspect, the higher purity may be determined by NMR or HPLC methods.

In one aspect of the method, the water content in the mobile phase is substantially in equilibrium with the water content of the column packing material before contacting the mobile phase to the packing material. In one variation, the packing material is silica gel.

In one aspect of the above, the method comprises the process of determining the water content of the mobile phase, adding water to the mobile phase to provide a water content in the mobile phase of about 15%, 10%, 5%, 4%, 3%, 2%, 1% wt/wt or less as a water wet mobile phase, and employing the water wet mobile phase in the column chromatographic separation method. In another aspect, the water content in the water wet mobile phase is about 15%, 10%, 5%, 4%, 3%, 2%, 1% wt/wt (water/solvent) or less of a single organic solvent mobile phase, or the mobile phase having more than one organic solvent. In another aspect, the water content in the mobile phase is the water saturated amount of a single solvent mobile phase, or the water saturated amount of one solvent in the mobile phase having a mixture of more than one solvent. In another aspect, the water content in the mobile phase is about 30%, 40%, 50%, 70%, 90% or about 100% of the water saturation amount of the mobile phase that comprises two or more organic solvents. In another aspect, the mobile phase is a mixture of two, three or four organic solvents. In another aspect of the above, the method further comprises the addition of at least one acid to the normal phase mobile phase. In another aspect, the acid is an organic acid. In one variation, the acid is selected from the group consisting of formic acid, acetic acid and propionic acid and mixtures thereof. In one aspect, the acid content in the mobile phase is about 0.01% to about 3% vol/vol; or about 0.01% to about 3% wt/wt. In another aspect, the acid content in the mobile phase is about 0.1% to about 2% vol/vol; or about 0.1% to about 2% wt/wt.

In another embodiment, there is provided a method for regenerating a previously processed packing material in a column of a column chromatographic separation apparatus for the separation of a composition comprising a mixture of components, wherein the packing material having an original equilibrium water content has been used in a chromatographic cycle for the separation of the composition using an organic mobile phase solvent, the method comprising an addition of a polar solvent having a higher dielectric constant than that of the mobile phase solvent, to the organic mobile phase solvent to form a regeneration solvent, cycling the regeneration solvent through the previously processed packing material, followed by cycling the organic mobile phase solvent through the packing material to regenerate the packing material substantially to its original equilibrium water content. In one aspect of the method, the packing material having an original equilibrium water content has been used in at least one or at least two chromatographic cycles. In one aspect of the method, the mobile phase solvent is a single solvent or a mixture of two or more solvents. In one aspect, the polar solvent is a polar aprotic solvent or polar protic solvent. In one aspect, the polar aprotic solvent is selected from the group consisting of THF, ethyl acetate, acetone, acetonitrile, DMF or mixtures thereof. In another aspect, the polar protic solvent is selected from the group consisting of methanol, ethanol, butanol, isopropanol, formic acid, acetic acid, water and mixtures thereof. In one aspect, the amount of regeneration solvent employed to regenerate the packing material is at least 100%, 150%, 200% or 300% vol/wt (solvent/packing material) of the packing material. In one aspect, the regeneration of the packing material (or normal phase chromatographic bed) results in a packing material that is at least 80%, 85%, 90% or 95% of its original equilibrium water content. In another aspect, the organic mobile phase solvent, the regeneration solvent or both the organic mobile phase solvent and the regeneration solvent comprises water. In another aspect, the water content in the organic mobile phase, the regeneration solvent or both the organic mobile phase solvent and the regeneration solvent, is about 15%, 10%, 5%, 4%, 3%, 2%, 1% wt/wt or less. In another aspect, the method further comprises the addition of at least one acid to the organic mobile phase, the regeneration solvent or both the organic mobile phase solvent and the regeneration solvent.

In another aspect, there is provided a chromatographic solvent composition for the chromatographic separation of a composition comprising a mixture of components using a silica gel packing material in a chromatographic column, wherein the chromatographic solvent composition has an equilibrium water content comparable such that the original equilibrium water content of the packing material, as commercially obtained, is maintained, the chromatographic solvent composition comprises a water content in the mobile phase of about 15%, 10%, 5%, 4%, 3%, 2%, 1% wt/wt or less. In one aspect, the solvent composition further comprises at least one acid in the solvent composition. In another aspect, the acid is selected from the group consisting of formic acid, acetic acid and propionic acid and mixtures thereof.

In another embodiment, there is provided a preparative chromatography column comprising a column tube having a proximal end and a distal end, a proximal distribution assembly comprising an inlet feature on an inlet piston in the proximal end of the column tube, a distal distribution assembly comprising an outlet feature on an outlet piston in the distal end of the column tube, a bed volume between the inlet piston and the outlet piston, wherein the inlet piston is coupled with a thrust washer, a disc spring washer, a disc spring washer guide and a compression cylinder, and wherein the inlet piston is biased against the disc spring for compressing the disc spring washer when the bed volume is filled with a stationary phase. In one aspect, the compression cylinder is coupled to a plurality of disc spring washers. In another aspect, the inlet piston is coupled with a plurality of thrust washers. In another aspect, the plurality of disc spring washers are stacked in series and/or in parallel. In another aspect, the preparative chromatography column, further comprising internal threading and threaded nuts for coupling of the proximal distribution assembly with the distal distribution assembly with the column tube. In another aspect of the above, the thrust washer and disc spring washer provides axial compression and/or maintains compression on the bed volume comprising chromatographic packing material.

In one embodiment, there is provided a method for controlling water content in normal phase mobile phases to improve peak shape and column performance. In another embodiment, there is provided the incorporation of a volume of a more polar solvent, the regeneration solvent followed by re-equilibration of the column with a volume of mobile phase between chromatographic runs or series of runs which cleans the normal phase chromatographic bed and returns it to a hydrated mobile phase stationary phase equilibrium suitable for the next chromatographic separation. In another embodiment, there is provided a preparative chromatography column design using disc spring washers to axially compress and/or maintain compression on the chromatographic bed. In one aspect of the above, the method for improving peak shape and column performance as provided above, is by the addition of water to normal phase mobile phases. In another aspect, there is provided a method for improving peak shape and column performance as above, by the addition of acid to normal phase mobile phases. In another aspect, there is provided a method for improving peak shape and column performance as above, by the addition of water and acid to normal phase mobile phases. In another aspect of the regeneration solution noted above, water is included in the mixture. In another aspect of the regeneration solution noted above, acid is included in the mixture. In another aspect of the regeneration solution noted above, water and acid are included in the mixture. In another aspect of the preparative chromatography column noted above, there is provided a plurality of disc spring washers. In another aspect of the preparative chromatography column noted above, the plurality of disc spring washers are stacked in series and/or in parallel. In another aspect of the preparative chromatography column noted above, there is internal threading and threaded nuts to attach the inlet and outlet assemblies to the column tube.

Description of FIG. 1:

The Figure is a cross section of one embodiment of the preparative column design including axial compression of the stationary phase with disc springs and the internal threaded design for holding the inlet and outlet of the column in place. In the figure, the length of the chromatographic bed is shortened considerably to reduce the size of the drawing and represents a bed length of about 15 cm. In one aspect of the application, the bed has a length of 50 cm.

Assembly normally begins with installation of the Outlet Piston 10 into the Column Tube 1. The Outlet Piston 10 has an Outlet Feature 3 for a standard tubing fitting with a solvent tube running from the Outlet Feature 3 to the Distribution Assembly 9. The Outlet Piston 10 is inserted in to the column Tube 1. The Outlet Piston is held in place by the Outlet Nut 11. There is an Inlet Feature 2 for a standard tubing fitting on the Inlet Piston 8 with a tube for solvent flow from the Inlet Feature 2 to the Distribution Assembly 9. The Inlet Piston 8 and the Distribution Assembly 9 are inserted in to the Column Tube 1. Behind the back of the Inlet Piston 8 are 4 each Thrust Washers 5, Disc Springs Washer 7 and a Disc Spring Guide 6. Back of the outside thrust washer 5 is the Compression Cylinder 13 which can be pressed on to compress the Disc Springs Washer 7 when the Bed Volume 12 is filled with stationary phase. With the Disc Springs Washer 7 compressed via the Compression Cylinder 13, Inlet Nut 4 is threaded into the Column Tube 1 and fixes the compression on the Disc Springs Washer 7.

Detailed Description of the Preparative Column:

An example embodiment of a design of a preparative column is briefly described as follows. Design considerations of a preparative column disc spring stack include size of the column, maximum operating pressure, mechanical strength of the stationary phase, and degree of settling of the stationary phase bed from use. In this example, assume the stationary phase bed diameter is 2.900 inch, the bed length is 19.7 inches, maximum operating pressure is 1,500 psi, the stationary phase is mechanically stable to 4,500 psi, and bed settling is 0.05 inches after initial compression. It should be noted that the stationary phase is compressible, its bed length decreases approximately 1 inch for every 1500 psi applied to it. When the bed is compressed to 3000 psi and compressed by approximately 2 inches, it is not likely to settle much more. The 2.900 in diameter of the bed is equal to a cross sectional area of 6.605 square inches. At the maximum operating pressure or mobile phase pressure of 1,500 psi this is 9,908 lb force. The disc spring washers should apply this 9908 lb force or greater to the bed at minimum deflection of 25%, i.e. after the bed is relaxed. The disc spring washers should not exceed the mechanical strength of the stationary phase at the maximum deflection of 75%, or approximately 29,722 lb force. The disc spring washers have to fit inside of the column tube. Christian Bauer disc spring washer number 92025201 meets these requirements when four disc spring washers are stacked in parallel and 2 sets of parallel stacks are stacked in series. The distance the springs will cause the piston to travel from maximum compression, 29,000 lb, to the minimum compression, 9,900 lb is 0.047 inches.

The design considerations for the internal threads are simply mechanical engineering calculations. In one aspect of the application, there is provided a method of using internal threads to hold the inlet and outlet of a preparative column in place. In this particular embodiment, the type of threads selected are standard buttress threads at 12 threads per inch and enough threads are used to ensure mechanical integrity at maximum bed compression and maximum operating pressure.

BRIEF DESCRIPTION OF THE DRAWINGS

FIG. 2. Table of Taxane Raw data, mobile phase, number of injections, retention times, peak widths in minutes at ½ height, and peak symmetry for Paclitaxel, Baccatin III and 10-Deacetyl Baccatin III.

FIG. 14. Table of Stevia Raw Data, mobile phase, number of injections, retention times, peak widths in minutes at ½ height, and peak symmetry for Rubusoside, Dulcoside A, Stevioside and Rebaudioside A.

FIG. 23: Table of Carotenoid Raw Data, mobile phase, number of injections, retention times and peak symmetry for Lutein and Zeaxanthin.

FIG. 24. Lutein and Zeaxanthin eluted with wet 10/4.5/5 EtOAc/heptanes/DCM mobile phase.

FIG. 25. Lutein and Zeaxanthin eluted with dry 10/4.5/5 EtOAc/heptanes/DCM mobile phase.

DESCRIPTION OF THE PREFERRED EMBODIMENTS

Figure 1:
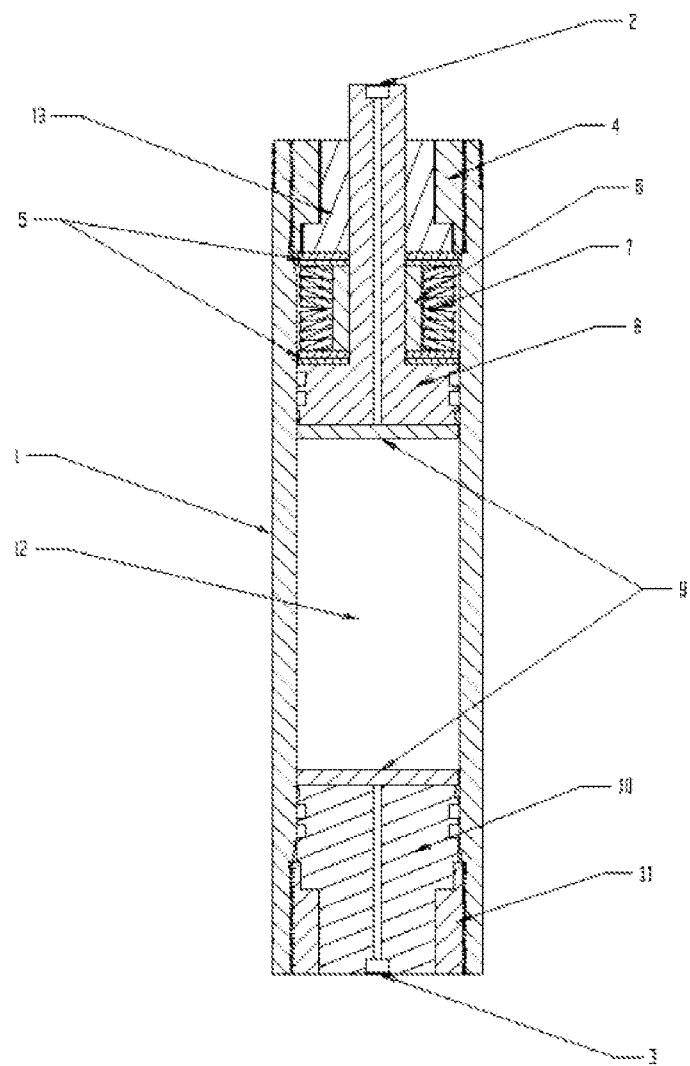
FIG. 1. A cross section view of the preparative column design showing internal threading and disc springs.

Normal Phase Chromatography Experimental:

As those familiar in the art of preparative chromatography know, a particular separation is composed of several things. These include the complexity and or degree of difficulty of the separation; the polarity of the mobile phase; the column performance or theoretical plates; the resolution of the peaks of interest; the peak shapes, i.e. symmetry, fronting or tailing, run to run reproducibility; and fouling of the column necessitating replacement of the column or its stationary phase. Normal phase chromatography in particular is not well understood by those who practice the art. One aspect of the application is to teach those familiar in the art the fundamentals for control of run to run reproducibility, with optimum peak shape, and with a regeneration of the column to restore and or maintain its performance without accumulated fouling. Run to run reproducibility is just that, minimal variation of retention time of the peaks of interest from run to run. Another way of saying this is predictability, the peaks elute when expected. Optimum peak shape is one that neither fronts nor tails. Regeneration is a cleaning and re-equilibration of a column between runs or series of runs that strips off the column the highly retained components in the mixture to be separated. Regeneration is best shown at preparative scale where the loading onto the column is very high relative to analytical loadings and the regeneration solution can be collected and the mass of the highly retained compounds measured, thus demonstrating the effectiveness of the regeneration. Illustration of these ideas are shown in an analytical column system with three mixtures; 1) moderately non-polar taxanes consisting of paclitaxel, baccatin III and 10-deacetyl baccatin III; 2) polar stevia glycosides consisting of rubusoside, dulcoside A, stevioside and rebausioside A; 3) very non-polar carotenoids consisting of luten and zeaxanthin. The analytical system used for analytical scale illustration of the concepts of this patent is an Agilent 1100 with a quatenary pump and VWD detector, degasser, column compartment and autosampler run with ChemStation software. The column is a Phemonenex part number 00G-4274-E0 Luna 5µ Silica (2) 100A serial number 477983-5.

Analytical Demonstration with Taxanes:

The method conditions are flow rate 1.5 mL/minute, column temperature of 20° C., detection at 280 nm, 10 µL injections. The mobile phase and regeneration solution compositions are as described below. The test probes are a mixture of approximately 2 mg/mL each of paclitaxel, baccatin III and 10-deacetyl baccatin III (10-DAB III) dissolved in ethyl acetate (EtOAc). For the mobile phases, a stock solution of 35/65 heptanes/ethyl acetate v/v was prepared. The ethyl acetate was HPLC grade and is <0.002% water. The heptanes were technical grade and filtered 0.45 µm. The solubility of water in EtOAc is approximately 3.3% at 20° C. and solubility of water in heptane is approximately 0.01%. In mixtures of heptanes and EtOAc the solubility of water is between these two values. From this stock solution a 0.64% v/v acetic acid, a 1% v/v water, and a 0.64% v/v acetic acid with 1.28% v/v water solutions were prepared. Acetic acid is selected because it is a weak organic acid not likely to degrade most compounds of interest during product recovery, it is volatile not leaving residual salts in the product, and traces that may be retained in the product are GRAS. The solutions containing water had excess non-miscible water at the bottoms of their respective vessels indicating that these solutions were saturated with water. The stock solution is also used in the demonstration as the dry, un-acidified mobile phase. The normal phase analytical column was equilibrated to the dry, un-acidified mobile phase. A series of injections were programmed as shown in Table 1A below. Table 1A shows the mobile phase used, the total number of injections, the injections used for the analyses and the average retention time (Average RT) with percent relative standard deviation (% RSD) and comments as appropriate below the average RT in the table for each of the three test probes. Table 1B is a continuation of the numerical analyses showing the peak symmetry values and % RSD for the three test probes. In all sets of injections the first injection is not included in the average and the % RSD analyses because the column was equilibrating from the previous injections. In two cases the equilibration took more than one injection and are indicated in the table below. Relative standard deviation is the standard deviation divided by the average times 100. The raw numerical data is in FIG. 2. The last three sets of injections include regeneration. The first is regeneration with 90/5/5/1 v/v EtOAc/methanol/water/acetic acid, the second is regeneration with 100 percent EtOAc, and the third is regeneration with 95/5 v/v EtOAc/methanol.

TABLE 1A

Mobile Phase used, total number of injections, injections used in the calculations, average RT with % RSD immediately below the average RT and comments as appropriate below the % RSD for paclitaxel, baccatin III and 10-DAB III.

| Mobile Phase | # of injections | injections used for anylases | Average RT % RSD comments Paclitaxel | Average RT % RSD comments Baccatin III | Average RT % RSD comments 10-DAB III |
|---|---|---|---|---|---|
| dry | 5 | 2-5 | 5.846 | 6.286 | 14.702 |
| | | | 0.118 | 0.087 | 0.064 |
| acidified | 5 | 2-5 | 5.103 | 5.924 | 13.359 |
| | | | 0.144 | 0.161 | 0.250 |
| dry | 5 | 2-5 | 5.478 | 6.291 | 14.470 |
| | | | 0.082 | 0.054 | 0.111 |
| wet | 5 | 2-5 | 5.098 | 5.689 | 11.968 |
| | | | 2.672 | 3.036 | 2.767 |
| | | | all RTs continuing to decrease | | |
| dry | 5 | 3-5 | 5.444 | 6.241 | 14.874 |
| | | | 0.193 | 0.080 | 0.044 |
| wet acidified | 5 | 2-5 | 4.692 | 5.237 | 10.478 |
| | | | 2.793 | 3.141 | 3.019 |
| | | | all RTs continuing to decrease | | |
| wet acidified regen 90/5/5/1 | 6 | 2-6 | 4.057 | 4.493 | 9.217 |
| | | | 4.916 | 4.966 | 4.698 |
| | | | all RTs continuing to decrease | | |
| wet acidified regen 100 EtOAc | 14 | 4-14 | 5.029 | 5.716 | 11.693 |
| | | | 0.032 | 0.041 | 0.035 |
| wet acidified regen 95/5 EtOAc/methanol | 10 | 2-10 | 4.796 | 5.660 | 11.532 |
| | | | 0.058 | 0.062 | 0.051 |

HP Chemstation computes symmetry with fronting being a value greater than one, perfect symmetry 1.000 and tailing having values less than one.

TABLE 1B

Mobile Phase used, total number of injections, injections used in the calculations, average symmetry with % RSD immediately below the average RT and comments as appropriate below the % RSD for paclitaxel, baccatin III and 10-DAB III.

| Mobile Phase | # of injections | injections used for analyses | Average Symmetry % RSD comments Paclitaxel | Average Symmetry % RSD comments Baccatin III | Average Symmetry % RSD comments 10-DAB III |
|---|---|---|---|---|---|
| dry | 5 | 2-5 | 0.286 | 0.250 | 0.123 |
| | | | 0.597 | 0.327 | 0.669 |
| acidified | 5 | 2-5 | 0.394 | 0.357 | 0.153 |
| | | | 0.903 | 0.981 | 0.979 |
| dry | 5 | 2-5 | 0.295 | 0.262 | 0.122 |
| | | | 0.650 | 0.825 | 0.000 |
| wet | 5 | 2-5 | 1.191 | 1.244 | 1.238 |
| | | | 21.401 | 25.441 | 26.869 |
| | | | fronting continuing to get worse | | |
| dry | 5 | 3-5 | 0.320 | 0.275 | 0.127 |
| | | | 2.083 | 1.828 | 1.635 |
| wet acidified | 5 | 2-5 | 0.878 | 0.866 | 0.838 |
| | | | 0.635 | 1.784 | 2.328 |

TABLE 1B-continued

Mobile Phase used, total number of injections, injections used in the calculations, average symmetry with % RSD immediately below the average RT and comments as appropriate below the % RSD for paclitaxel, baccatin III and 10-DAB III.

| Mobile Phase | # of injections | injections used for analyses | Average Symmetry % RSD comments Paclitaxel | Average Symmetry % RSD comments Baccatin III | Average Symmetry % RSD comments 10-DAB III |
|---|---|---|---|---|---|
| wet acidified regen 95/5/5/1 | 6 | 2-6 | 1.363 4.728 fronting | 1.493 1.483 continuing to get | 1.820 3.149 worse |
| wet acidified regen 100 EtOAc | 14 | 4-14 | 0.871 0.191 | 0.835 0.221 | 0.780 0.287 |
| wet acidified regen 95/5 EtOAc/methanol | 10 | 2-10 | 0.867 0.252 | 0.831 0.248 | 0.775 0.428 |

Figure 3:
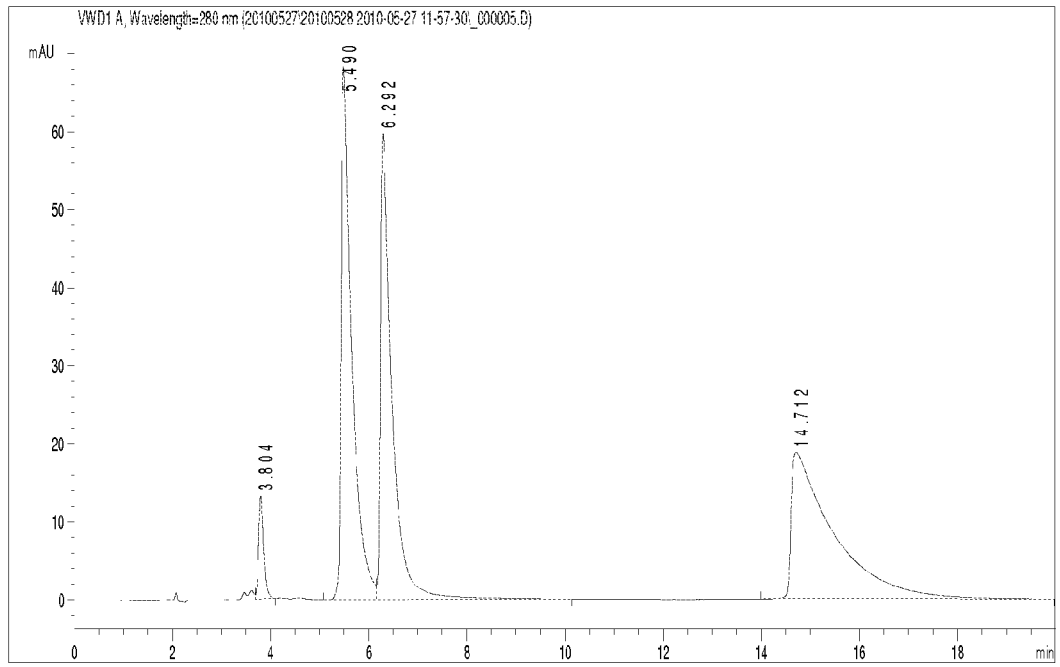
FIG. 3. Paclitaxel, Baccatin III and 10-Deacetyl baccatin III eluted with dry 35/65 heptane/ethyl acetate.
Figure 4:
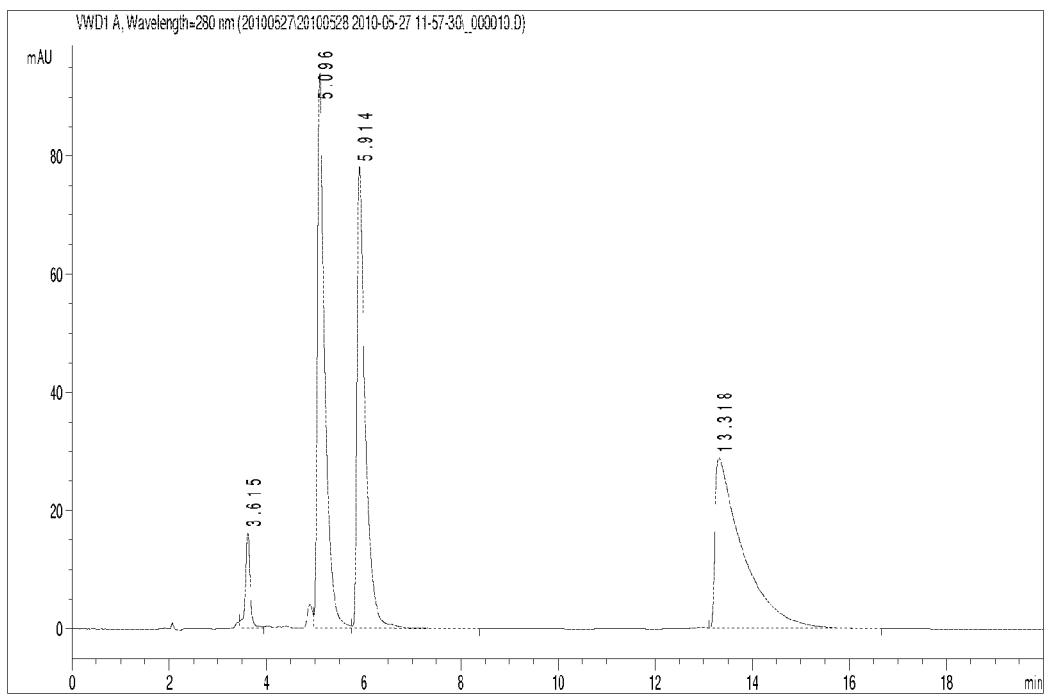
FIG. 4. Paclitaxel, Baccatin III and 10-Deacetyl baccatin III eluted with acidified 35/65 heptane/ethyl acetate.
Figure 5:
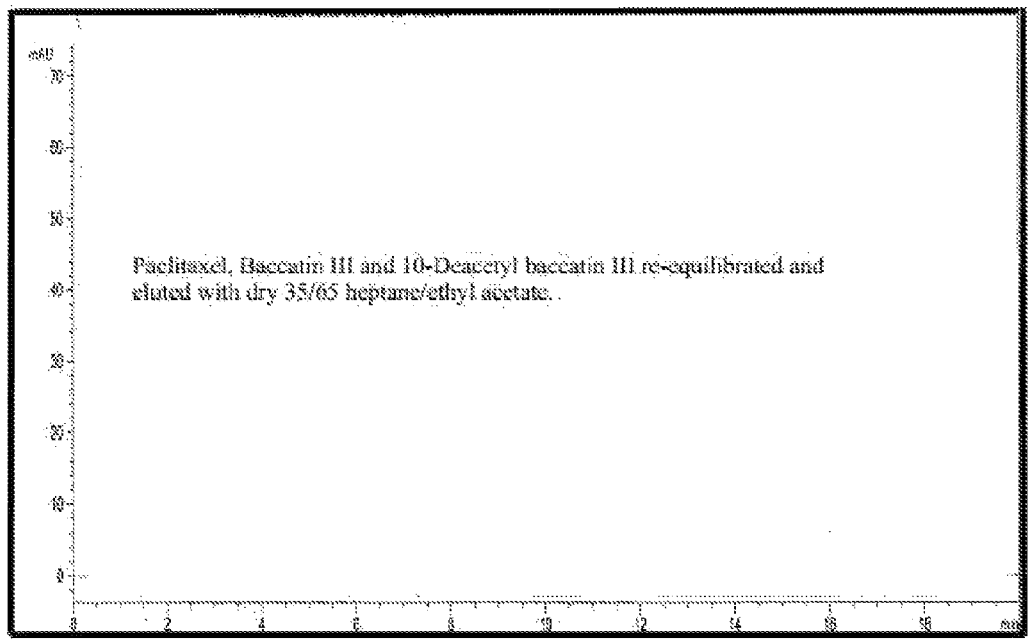
FIG. 5. Paclitaxel, Baccatin III and 10-Deacetyl baccatin III re-equilibrated and eluted with dry 35/65 heptane/ethyl acetate.
Figure 6:
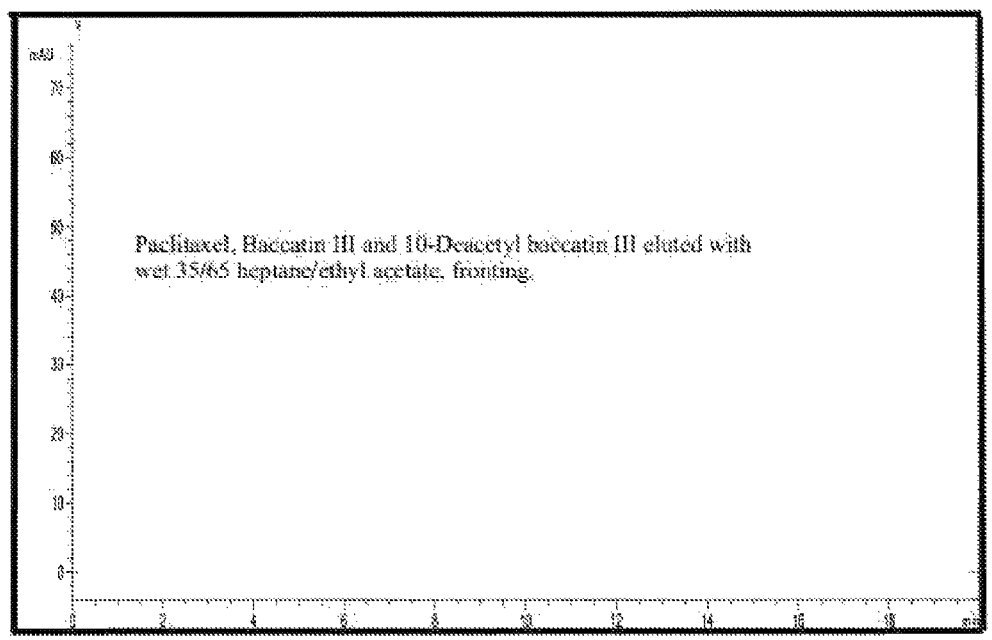
FIG. 6. Paclitaxel, Baccatin III and 10-Deacetyl baccatin III eluted with wet 35/65 heptane/ethyl acetate, fronting.
Figure 7:
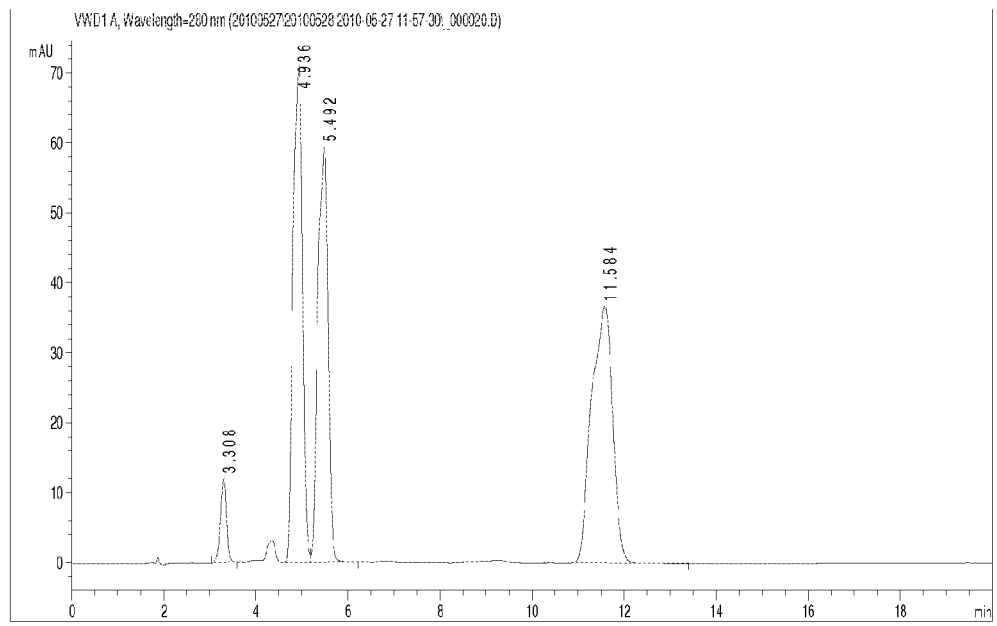
FIG. 7. Paclitaxel, Baccatin III and 10-Deacetyl baccatin III eluted with wet 35/65 heptane/ethyl acetate, more fronting.
Figure 8:
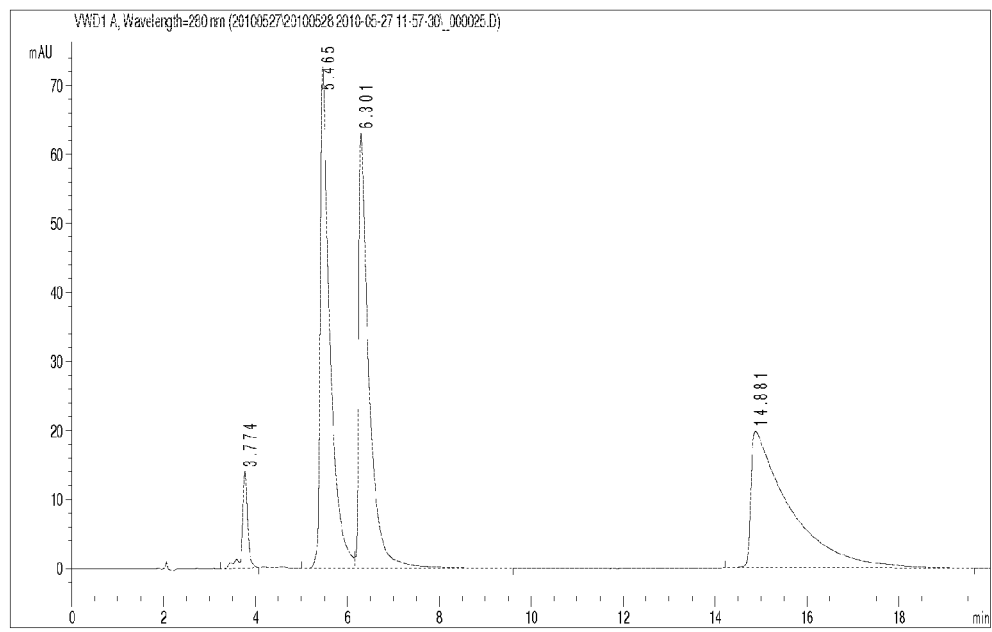
FIG. 8. Paclitaxel, Baccatin III and 10-Deacetyl baccatin III re-equilibrated and eluted with dry 35/65 heptane/ethyl acetate.
Figure 9:
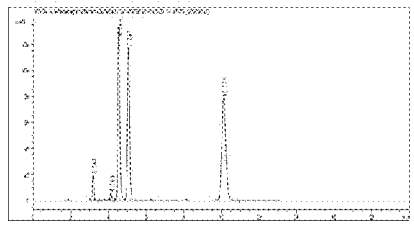
FIG. 9. Paclitaxel, Baccatin III and 10-Deacetyl baccatin III eluted with wet acidified 35/65 heptane/ethyl acetate.
Figure 10:
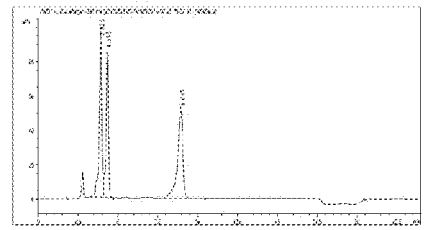
FIG. 10. Paclitaxel, Baccatin III and 10-Deacetyl baccatin III eluted with wet acidified 35/65 heptane/ethyl acetate after a series of regenerations containing too much water.
Figure 11:
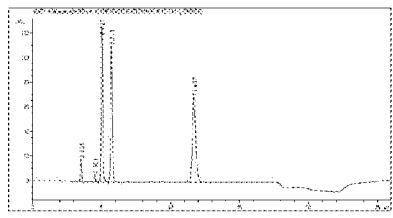
FIG. 11. Paclitaxel, Baccatin III and 10-Deacetyl baccatin III eluted with wet acidified 35/65 heptane/ethyl acetate after a series of regenerations with dry ethyl acetate.
Figure 12:
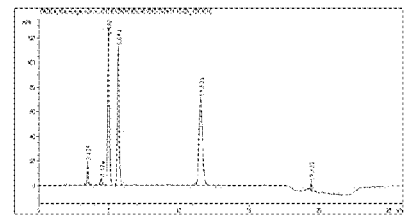
FIG. 12. Paclitaxel, Baccatin III and 10-Deacetyl baccatin III eluted with wet acidified 35/65 heptane/ethyl acetate after a series of regenerations with 95/5 v/v ethyl acetate/methanol.
Figure 13:
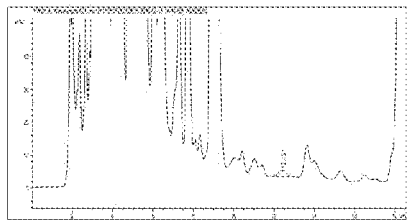
FIG. 13. Taxus Extract eluted with wet acidified 50/50 heptane/ethyl acetate with regeneration with 95/5 v/v ethyl acetate/methanol. The integrated peak RT 12.431 is paclitaxel, verified by standard additions.

The above data show that a normal phase silica column can be equilibrated to a dry un-acidified mobile phase which during multiple injections produces consistent retention times and symmetries for the test probes. The symmetries are poor showing tailing. See FIG. 3. The column can then be equilibrated to a mobile phase containing acetic acid and the retention times and symmetries are consistent, the retention times decrease slightly and the symmetries improve slightly. See FIG. 4. The column can be re-equilibrated to the dry un-acidified mobile phase, with the retention times and symmetries consistent and returning to the original values more or less. See FIG. 5. The column can then be run with a wet mobile phase which doesn't come to equilibrium during 5 injections with the retention times decreasing and symmetries fronting more and more. See FIGS. 6 and 7, note that these are injections 4 and 5 of the series and the RTs are continuing to change. The column can be brought back to equilibrium with the dry un-acidified mobile phase with the retention times and symmetries consistent and returning to the original values more or less. See FIG. 8. Then the column can be run with a wet acidified mobile phase and the retention times are consistent and the peak symmetries are good. See FIG. 9. Next, the introduction of a regeneration step at the end of a run, a small volume of a more polar solution intended to clean the column followed by a period of re-equilibration to the mobile phase. A regeneration solution 95/5/5/1 is too wet to re-equilibrate with this mobile phase and produces diminishing retention times and increasingly fronting symmetries. See FIG. 10. A regeneration solution of ethyl acetate or 95/5 ethyl acetate/methanol can be introduced with very consistent retention times and symmetries with the symmetries approaching 1.000. See FIGS. 11 and 12. Taxus x media 'Hicksii' extract was analyzed using the preparative scale mobile phase, wet acidified 50/50 heptanes/EtOAc. See FIG. 13. The paclitaxel peak was verified by standard additions of paclitaxel.

One skilled in the art can quickly see that this information can be used to facilitate the development of mobile phases for use in preparative normal phase separations that give predictable and reproducible retention times and a method for cleaning or regeneration of a normal phase column. Additionally, this information can also be used to facilitate development of analytical normal phase separations which are particularly useful as orthaganol analyses to the usual derivatized silica moiety ("Reverse Phase") analyses as part of a procedure employed to verify peak purities in pharmaceutical or nutraceutical applications.

Analytical Demonstration with Stevia Glycosides:

The analytical method conditions for this demonstration are: flow 1.5 mL/min, column temperature 20° C., detection at 210 nm, 10 μL injection volume. Mobile phase and regeneration composition are described below. The test mixture is approximately 2.5 mg/mL each of the Stevia glycosides Rubusoside, Dulcoside A, Stevioside and Rebaudioside A (Reb A) dissolved in 8/1/5 methanol/water/methyl tert butyl ether (MTBE). A stock solution of 100/20 v/v MTBE/methanol was prepared. From this stock solution, solutions of 100/20/0.1 v/v MTBE/methanol/acetic acid, 100/20/10 v/v MTBE/methanol/water, 100/20/2/0.1 v/v MTBE/methanol/water/acetic acid were prepared. The stock solution is also used in the demonstration as the dry, un-acidified mobile phase. A regeneration solution of 50/50 MTBE/methanol was also prepared. The normal phase analytical column was equilibrated to the dry, un-acidified mobile phase. A series of injections were programmed as shown in Table 2A below. The raw numerical data are found in FIG. 14.

TABLE 2A

Mobile phase, number of injections, injections used for the numerical analyses with Average retention time and % RSD for Rubusoside, Dulcoside A, Stevioside and Rebaudioside A.

| Mobile Phase | # of injections | injections used for analyses | Average RT % RSD comments Rubusoside | Average RT % RSD comments Dulcoside A | Average RT % RSD comments Stevioside | Average RT % RSD comments Reb A |
|---|---|---|---|---|---|---|
| 100/20 | 7 | 1-7 | 6.654 0.318 | 10.793 0.382 | 17.771 0.416 | 26.658 0.497 |
| 100/20/0.1 | 5 | 2-5 | 6.341 0.147 | 10.088 0.179 | 16.443 0.189 | 24.668 0.170 |
| 100/20 | 5 | 2-5 | 6.569 0.153 | 10.594 0.268 | 17.377 0.381 | 25.982 0.453 |

TABLE 2A-continued

Mobile phase, number of injections, injections used for the numerical analyses with Average retention time and % RSD for Rubusoside, Dulcoside A, Stevioside and Rebaudioside A.

| Mobile Phase | # of injections | injections used for analyses | Average RT % RSD comments Rubusoside | Average RT % RSD comments Dulcoside A | Average RT % RSD comments Stevioside | Average RT % RSD comments Reb A |
|---|---|---|---|---|---|---|
| 100/20/10 | 5 | 2-5 | 4.339 | 5.531 | 7.055 | 9.852 |
| | | | 0.029 | 0.116 | 0.189 | 0.286 |
| 100/20 | 5 | 2-5 | 6.896 | 11.327 | 18.852 | 28.528 |
| | | | 0.321 | 0.470 | 0.596 | 0.672 |
| 100/20/2/0.1 | 5 | 2-5 | 5.107 | 7.210 | 10.982 | 16.282 |
| | | | 0.042 | 0.033 | 0.049 | 0.112 |
| 100/20/2/0.1 regen 50/50 MTBE/methanol | 6 | 1-6 | 4.833 0.144 | 6.569 0.146 | 9.584 0.124 | 13.814 0.145 |

HP Chemstation computes symmetry with fronting being a value greater than one, perfect symmetry 1.000 and tailing having values less than one.

TABLE 2B

Mobile phase, number of injections, injections used for the numerical analyses with Average Symmetry and % RSD for Rubusoside, Dulcoside A, Stevioside, and Rebaudioside A.

| Mobile Phase | # of injections | injections used for analyses | Average Symmetry % RSD comments Rubusoside | Average Symmetry % RSD comments Dulcoside A | Average Symmetry % RSD comments Stevioside | Average Symmetry % RSD comments Reb A |
|---|---|---|---|---|---|---|
| 100/20 | 7 | 1-7 | 0.642 | 0.469 | 0.397 | 0.667 |
| | | | 1.181 | 2.362 | 0.657 | 3.433 |
| 100/20/0.1 | 5 | 2-5 | 0.669 | 0.511 | 0.459 | 0.760 |
| | | | 1.518 | 0.434 | 1.957 | 0.473 |
| 100/20 | 5 | 2-5 | 0.632 | 0.463 | 0.392 | 0.653 |
| | | | 0.299 | 0.176 | 0.244 | 0.375 |
| 100/20/10 | 5 | 2-5 | 1.282 | 1.183 | 1.172 | 1.220 |
| | | | 1.405 | 1.206 | 2.301 | 2.568 |
| 100/20 | 5 | 2-5 | 0.605 | 0.441 | 0.360 | 0.602 |
| | | | 1.580 | 4.144 | 2.536 | 5.521 |
| 100/20/2/0.1 | 5 | 2-5 | 0.833 | 0.699 | 0.756 | 0.911 |
| | | | 0.646 | 2.641 | 4.091 | 3.873 |
| 100/20/2/0.1 regen 50/50 MTBE/methanol | 6 | 1-6 | 0.909 0.648 | 0.841 0.398 | 0.867 1.000 | 0.943 3.832 |

Figure 15:
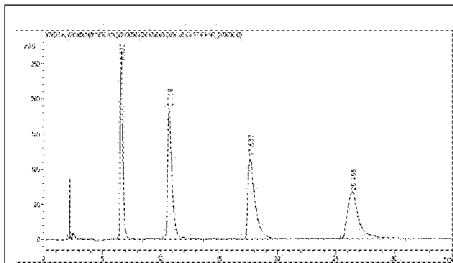
FIG. 15. Stevia Mixture Rubusoside, Dulcoside A, Stevioside and Rebaudioside A eluted with dry 100/20 MTBE/methanol.
Figure 16:
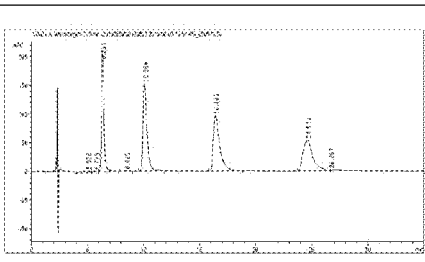
FIG. 16. Stevia Mixture Rubusoside, Dulcoside A, Stevioside and Rebaudioside A eluted with dry 100/20/0.1 MTBE/methanol/acetic acid.
Figure 17:
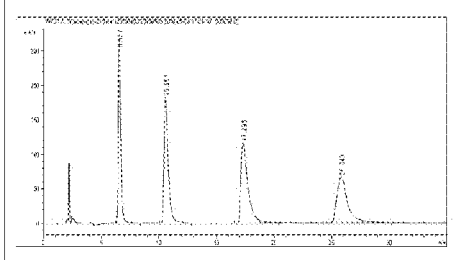
FIG. 17. Stevia Mixture Rubusoside, Dulcoside A, Stevioside and Rebaudioside A re-equilibrated and eluted with dry 100/20 MTBE/methanol.
Figure 18:
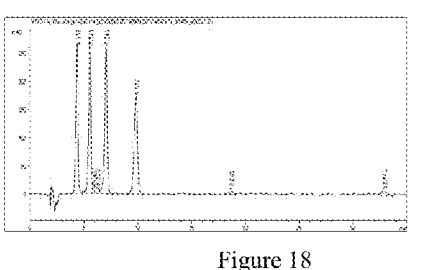
FIG. 18. Stevia Mixture Rubusoside, Dulcoside A, Stevioside and Rebaudioside A eluted with 100/20/10 MTBE/methanol/water.
Figure 19:
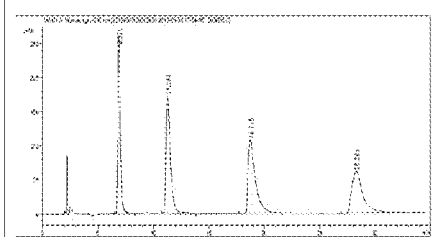
FIG. 19. Stevia Mixture Rubusoside, Dulcoside A, Stevioside and Rebaudioside A re-equilibrated and eluted with dry 100/20 MTBE/methanol.
Figure 20:
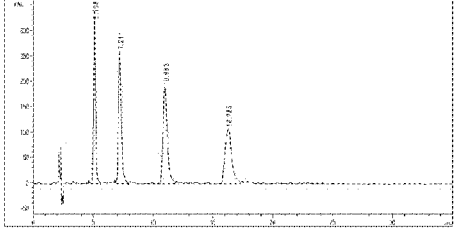
FIG. 20. Stevia Mixture Rubusoside, Dulcoside A, Stevioside and Rebaudioside A eluted with 100/20/2/0.1 MTBE/methanol/water/acetic acid.
Figure 21:
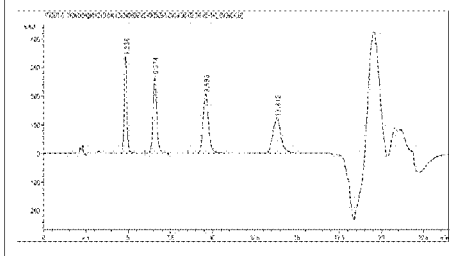
FIG. 21. Stevia Mixture Rubusoside, Dulcoside A, Stevioside and Rebaudioside A eluted with 100/20/2/0.1 MTBE/methanol/water/acetic acid and with a 50/50 MTBE/methanol regeneration.
Figure 22:
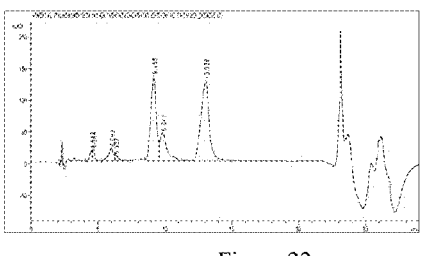
FIG. 22. Stevia Extract eluted with 100/20/2/0.1 MTBE/methanol/water/acetic acid and with a 50/50 MTBE/methanol regeneration. The three largest peaks are in order of elution Stevioside, Rebaudioside C and Rebaudioside A.
Figure 34:
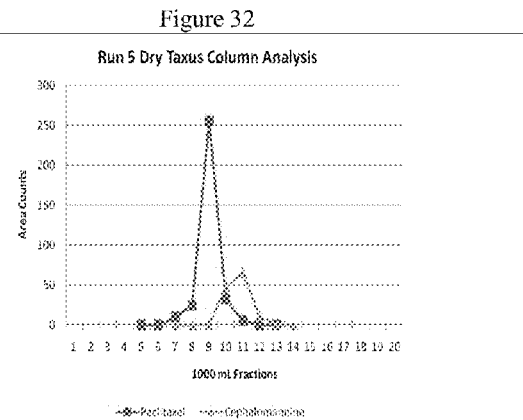
FIG. 34. Column analysis of fractions from Run 5 for paclitaxel and cephalomannine Eluted with dry un-acidified mobile phase.
Figure 35:
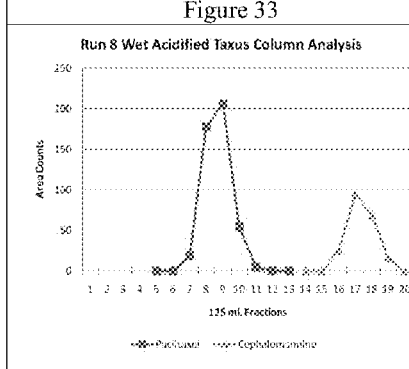
FIG. 35. Column analysis of fractions from Run 8 for paclitaxel and cephalomannine Eluted with wet acidified mobile phase.

The same phenomena are observed with the normal phase column with these more polar analytes and more polar mobile phases. The column can be equilibrated with a dry un-acidified mobile phase and consistent retention times and symmetries are seen. The symmetries are again tailing badly. See FIG. 15. The addition of acid reduces retention time slightly and improves symmetry slightly. See FIG. 16. The column can be re-equilibrated with the dry un-acidified mobile phase producing more or less the same retention times and symmetries. See FIG. 17. The addition of too much water reduces the retention times significantly due to the increase of polarity of the mobile phase, but also causes the peaks to front badly. See FIG. 18. The column can be again re-equilibrated with the dry un-acidified mobile phase producing more or less the same retention times and symmetries. See FIG. 19. The addition of an adequate amount of water with acetic acid produces consistent retention times and good peak symmetries. See FIG. 20. The further inclusion of a more polar regeneration solvent into the method reduces retention times a little but the peak symmetries are further improved. See FIG. 21. A Stevia extract was analyzed with the wet mobile phase. See FIG. 22. The three predominate peaks are from left to right Stevioside, Rebaudioside C and Rebaudioside A. Comparing this analysis to the Preparative Column of Stevia Glycoside, FIG. 34, shows that the analytical result is predictive of the preparative result. Stevioside and Rebaudioside C are not well resolved and they are well resolved from Rebaudioside A.

Analytical Demonstration with Carotenoids:

The analytical method conditions for this demonstration are: flow 1.5 mL/min, column temperature 20° C., detection at 440 nm, 2 µL injection volume. Mobile phase and regeneration composition are described below. The test mixture is approximately 0.5 mg/mL of a mixture of lutein, approximately 90% by area and about 6% by area zeaxanthin dissolved in methylene chloride (DCM). A stock solution of 10/4.5/5 v/v EtOAc/heptanes/DCM was prepared. From this stock solution, a portion was saturated with approximately 0.5 mL water. There was an excess of water in this wet mobile phase. A regeneration solution of 50/50 EtOAc/DCM was also prepared. The stock solution is used in the demonstration as the dry mobile phase. A series of injections were programmed as shown in Table 3A below. The raw numerical data are found in FIG. 23.

TABLE 3A

Mobile phase, number of injections, injections used for the numerical analyses with Average retention time and % RSD for Lutein and Zeaxanthin.

| Mobile Phase | # of injections | injections used for analyses | Average RT % RSD comments Lutein | Average RT % RSD comments Zeaxanthin |
|---|---|---|---|---|
| wet | 5 | 3-5 | 4.134 0.63 | 4.476 0.75 |
| dry | 6 | 2-6 | 4.721 0.14 | 5.235 0.17 |
| wet | 4 | 2-4 | 4.175 0.11 | 4.520 0.11 |

TABLE 3B

Mobile phase, number of injections, injections used for the numerical analyses with Average Symmetry and % RSD for Lutein and Zeaxanthin.

| Mobile Phase | # of injections | injections used for analyses | Average Symmetry % RSD comments Lutein | Average Symmetry % RSD comments Zeaxanthin |
|---|---|---|---|---|
| wet | 5 | 3-5 | 0.904 0.17 | 0.891 0.11 |
| dry | 6 | 2-6 | 0.907 0.20 | 0.934 1.88 |
| wet | 4 | 2-4 | 0.902 0.11 | 0.838 0.93 |

This series starts with the wet mobile phase injections followed by dry mobile phase injections, then back to the wet mobile phase. The same phenomena are observed with the normal phase column with these more non-polar analytes and more non-polar mobile phases. For both the wet and dry mobile phases, the retention times stabilize with small % RSDs. The retention times increase with the dry mobile phase. With these compounds the peak symmetries are not affected by drying of the column and the data suggest that the symmetries of zeaxanthin improve with the dry mobile phase. Additionally, the difference of retention time increases with the dry mobile phase from about 0.34 minutes to 0.51 minutes as well, suggesting that a dry mobile phase may in fact be better for this separation. The point here is that by paying attention to hydration, normal phase separations can be controlled, reproducible, and optimized. Typical chromatograms of this separation with wet and dry mobile phases are shown in FIGS. 24 and 25 respectively.

Figure 26:
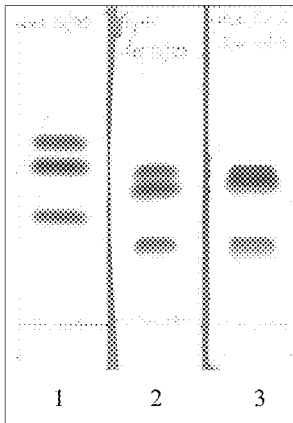
FIG. 26. In order from left to right, 1) taxanes (paclitaxel, baccatin III, 10-deacetyl baccatin III) on a plate equilibrated to the ambient environment eluted with wa 10/90 heptanes/EtOAc, 2) taxanes on a plate equilibrated to the ambient environment eluted with dry 10/90 heptanes/EtOAc, 3) taxanes on a plate dried in an oven at 100° C. for an hour then spotted and eluted with wa 10/90 heptanes/EtOAc.

TLC Demonstrations:

The TLCs used are EMD part number 5629-5; HPTLC Silica Gel 60 $F_{254}$ 10×10 cm; Lot HX955163. The TLCs are cut from the 10×10 cm plates as needed. There are three taxane TLC plates, see FIG. 26; 1) taxanes (paclitaxel, baccatin III, 10-deacetyl baccatin III) on a plate equilibrated to the ambient environment eluted with wa 10/90 heptanes/EtOAc, 2) taxanes on a plate equilibrated to the ambient environment eluted with dry 10/90 heptanes/EtOAc, 3) taxanes on a plate dried in an oven at 100° C. for an hour eluted with wa 10/90 heptanes/EtOAc. Similar to the analytical demonstrations, the wet acidified mobile phase elutes the compounds quicker with better resolution than the dry mobile phase. The plate which was dried in the oven before spotting and elution with the dry mobile phase shows similar rate of elution to that of the non-dried plate and dry solvent but the resolution between paclitaxel and baccatin III is even less.

Figure 27:
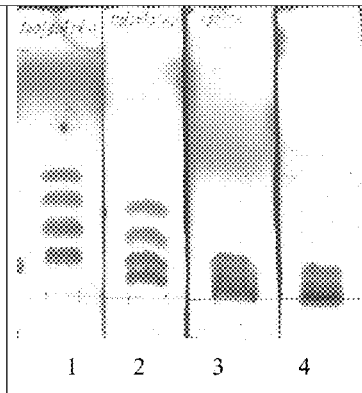
FIG. 27. In order from left to right, 1) stevia glycosides (rubusoside, dulcoside A, stevioside, and rebaudioside A) on a plate equilibrated to the ambient environment eluted with 100/30/10/0.1 MTBE/methanol/water/acetic acid, 2) stevia glycosides on a plate equilibrated to the ambient environment eluted with 100/30/2/0.1 MTBE/methanol/water/acetic acid, 3) stevia glycosides on a plate equilibrated to the ambient environment eluted with 100/30 MTBE/methanol, 4) stevia glycosides on a plate dried in an oven at 100° C. for an hour then spotted and eluted with100/30 MTBE/methanol.

There are four stevia glycoside TLC plates, see FIG. 27; 1) stevia glycosides (rubusoside, dulcoside A, stevioside, and rebaudioside A) on a plate equilibrated to the ambient environment eluted with 100/30/10/0.1 MTBE/methanol/water/acetic acid, 2) stevia glycosides on a plate equilibrated to the ambient environment eluted with 100/30/2/0.1 MTBE/methanol/water/acetic acid, 3) stevia glycosides on a plate equilibrated to the ambient environment eluted with 100/30 MTBE/methanol, 4) stevia glycosides on a plate dried in an oven at 100° C. for an hour then spotted and eluted with 100/30 MTBE/methanol. Similar to the analytical demonstrations, the wet acidified mobile phases, plates one and two, elute the compounds quicker with better resolution than the dry mobile phase, plate 3. Plate 4 which was dried in the oven before spotting and elution with the dry mobile phase shows an even lower rate of elution to that of the non-dried plate and dry solvent and that the compounds are even less separated.

Effects of Column Hydration on Routine Normal Phase Preparative Scale Column Performance Tests:

The preparative system used to illustrate these concepts with taxanes is an embodiment of the column design described elsewhere in this application, nominally 7.5 cm internal diameter x 50 cm bed length packed with 1 kg Kromasil 10 μm spherical 60 Å silica gel; a Prep 250 pump, a pulse dampener (patent pending), a 1.2 mL load loop, a Hyperquan VWD detector and a Kipp and Zonen flatbed chart recorder.

A normal phase preparative scale column performance test has been developed and employed to evaluate the quality of a newly packed column as well as to monitor the columns' performance as it is used for various projects. This performance test consists of two test probes, toluene and ethyl paraben, dissolved in ethyl acetate. The mobile phase is 80/20 heptane/wa ethyl acetate (2% v/v water and 1% v/v acetic acid). The wa ethyl acetate is prepared and allowed to equilibrate before being added to the heptane after which the mixture is allowed to equilibrate and clear as the excess water is separated to the bottom of the vessel. The flow is 250 mL/min, detection is at 254 nm with the chart speed at 0.5 mm/second. From measurements of the UV trace the following standard calculations are used for theoretical plates/meter (N/m) and Asymmetry ($A_s$):

$$N/m = 5.54(t_r/w_{1/2})^2$$

Where: $t_r$=time the peak is retained
$w_{1/2}$=width of the peak at ½ height $$A_s = B/A$$

Where: A=width of the front of the peak from centerline at 10% of the peak height
B=width of the back of the peak from centerline at 10% of the peak height This column has had seven performance tests usually several months apart and produced average results of the two test probes of 18,000 to 21,000 N/m and 1.3 to 1.6 $A_s$. The results of performance test number seven are show in the table below. The column was thoroughly dried with 6 column volumes (cv, 1 cv is 2135 mLs) of 50/50 ethyl acetate/methanol followed by a 2 cv equilibration with the performance test mobile phase 80/20 heptane/wa ethyl acetate followed by two performance tests, numbers eight and nine. These tests showed an average of the two probes 11,501 and 7,775 N/m respectively and $A_s$ ethyl paraben 0.7. Clearly the column's performance has apparently degraded.

TABLE 4

Column Performance Test Number, N/m and $A_s$ for Toluene and Ethyl Paraben and average N/m of Toluene and Ethyl Paraben.

| Performance Test Number | Toluene N/m | $A_s$ | Ethyl Paraben N/m | $A_s$ | Average N/m |
|---|---|---|---|---|---|
| 7 | 19,679 | 1.4 | 20,092 | 1.4 | 19,885 |
| 8 | 17,231 | 1.4 | 5,770 | 0.7 | 11,501 |
| 9 | 11,845 | 1.4 | 3,705 | 0.7 | 7,775 |
| 10 | 25,841 | 1.5 | 14,292 | 1.2 | 20,068 |

The column was again dried with four cv of 90/10 ethyl acetate/methanol. The column was then equilibrated with 4 cv of wa ethyl acetate (2% v/v water and 1% v/v acetic acid). Then equilibrated with 1.5 cv of the performance test mobile phase 80/20 heptane/wa ethyl acetate followed by a performance test, number ten. The average N/m of the test probes is 20,068. However, the ethyl paraben N/m is still low. This result clearly demonstrates that the apparent performance degradation is due to dehydration of the column, not due to a physical or mechanical change in the bed structure.

Figure 28:
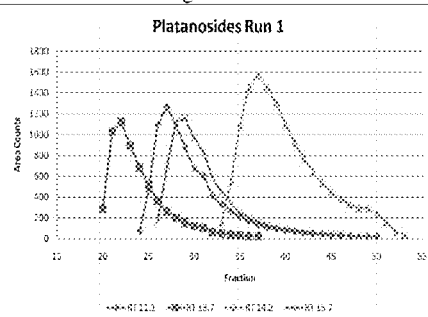
FIG. 28. Run 1 Column Analysis of Platanoside isomers showing tailing.
Figure 29:
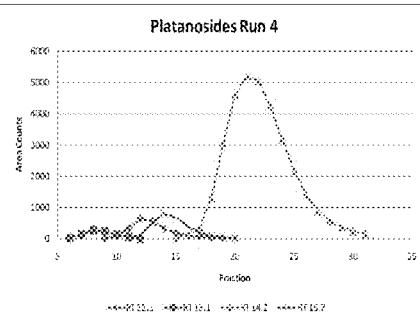
FIG. 29. Run 4 Column Analysis of Platanoside isomers showing reduced tailing.

Following performance test ten, the column was equilibrated to 80/20 wa methyl tertiary-butyl ether (wa MTBE)/n-heptane for the purification of platanoside isomers. The wa MTBE (1% v/v water and 0.5% v/v acetic acid) was prepared and allowed to equilibrate before being added to the heptane after which the mixture is allowed to equilibrate and clear as the excess water is separated to the bottom of the vessel. The flow was 250 mL/min, detection was at 313 nm with 125 mL fractions collected and analyzed by HPLC. The first run showed tailing of the platanoside isomers indicating that the appropriate hydration of the column for this separation has not yet been achieved, see FIG. 28. The column was then regenerated using ½ cv of 83/8/9 ethyl acetate/water/methanol followed by equilibration with the 80/20 wa MTBE/n-heptane mobile phase and a second column run in the same manner as the first. The HPLC analysis of the second run showed a decreased tailing of the compounds. A third run was performed and regenerated in the same manner. The HPLC analysis of the third run showed again a further decreased tailing of the compounds from the second run. A fourth run was performed in the same manner. The HPLC analysis of the fourth run showed continued decrease of tailing of the compounds indicating that the appropriate hydration of the column is being approached, see FIG. 29.

Preparative Scale Taxane Demonstration:

The preparative system used to illustrate these concepts with taxanes is an embodiment of the column design described elsewhere in this application, nominally 7.5 cm internal diameter×50 cm bed length packed with 1 kg Kromasil 10 μm spherical 60 Å silica gel; a Prep 250 pump, a pulse dampener (patent pending), a 1.2 mL load loop or a 3.2 cm internal diameter×13 cm length load column, a Hyperquan VWD detector and a Kipp and Zonen flatbed chart recorder.

This demonstration is performed using two materials. First, reagent grade paclitaxel to show retention time, peak shape and theoretical plates. Second, an extract of Taxus x Media "Hicksii" containing approximately 0.8% by weight paclitaxel to provide an example of a well known difficult isolation and the separation of paclitaxel from cephalomannine. The extract was passed through an adsorbent column comprised of silica and powdered activated carbon to remove very highly retained materials and chlorophylls. The extract was then concentrated and dried onto diatomaceous earth (DE). Portions of the DE containing 4 grams (approximately 30 mg of paclitaxel) of extract solids were weighed and packed into a load column for each Taxus Extract run.

Determination of mobile phase composition for a preparative normal phase separation can be accomplished by using an analytical silica column and system, however in practice this usually requires the changing of an analytical system from a reversed phase setup to a normal phase setup and back. Determination of the mobile phase by TLC avoids this. TLC's were run with paclitaxel and retardation factors ($R_f$) calculated for wet acidified (wa) 46/54, 50/50, and 55/45 mixtures of heptanes/EtOAc. Mobile phases which give $R_f$s of between 0.15 and 0.2 are usually acceptable for scale up to preparative separations. The $R_f$s were 0.19, 0.14, and 0.09 respectively. The wa 50/50 producing an $R_f$ of 0.14 was selected for the preparative scale mobile phase. This mobile phase was then tested on the analytical system with the paclitaxel standard material and the Taxus extract. Paclitaxel was found to elute at 4.55 column volumes (cvs). Preparative separations are usually performed with the compounds of interest retained on the column between 3-5 cvs.

A solution of 30 mg/mL paclitaxel in EtOAc was prepared, loaded into a 1.2 mL load loop, injected onto the column and eluted with wet acidified 50/50 heptanes/EtOAc mobile phase (50/50/1/0.5 heptanes/EtOAc/water/acetic acid or dry un-acidified 50/50 heptanes/EtOAc. This quantity of paclitaxel is used because it is comparable to the quantity of paclitaxel in the Taxus Extract runs. A UV trace was collected at 280 nm for each run. The flow rate and chart speed for all runs were 250 mL/minute (apparent velocity of 6 cm/minute) and 0.2 mm/sec. This was performed four times, Runs 1, 4, 6 and 7. The column for Runs 1, 6 and 7 was equilibrated and eluted with the wet acidified mobile phase. The column for Run 4 was dried by passing 5 cv of 95/5 technical grade EtOAc/technical grade methanol then equilibrated with 2 cv of the dry mobile phase then eluted with the dry mobile phase. Table 5 below summarizes the paclitaxel retention time in mm from the UV trace, column volumes (this column volume is 2135 mLs), peak width at ½ height in mm, theoretical plates/meter (N/m), and symmetry. Symmetry is measured at 10% of peak height, front width/back width.

TABLE 5

Run number, Paclitaxel Retention Time in mm, Paclitaxel Retention Time in cvs, Peak width at ½ height, Theoretical plates/meter, and Symmetry for each of the 30 mg Paclitaxel runs.

| Run # | Pac RT, mm | Pac RT, cvs | Width, mm | N/m | Symmetry |
|---|---|---|---|---|---|
| 1 | 171 | 3.3 | 4.5 | 16,000 | 0.89 |
| 4 | 254 | 5.0 | 41.0 | 425 | 0.18 |
| 6 | 189 | 3.7 | 5.0 | 15,832 | 0.85 |
| 7 | 193 | 3.8 | 5.1 | 15,868 | 0.90 |

Figure 30:
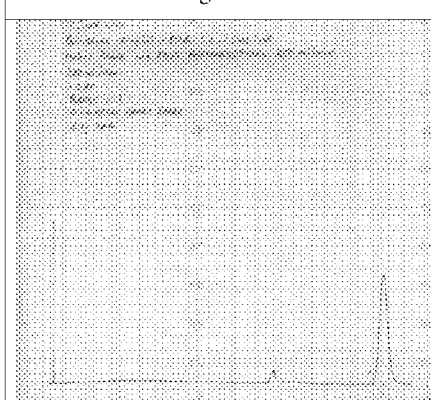
FIG. 30. UV trace at 280 nm of a 30 mg load of paclitaxel onto a preparative column and eluted with wa 50/50 heptanes/EtOAc. The paclitaxel peak is the later (bottom) tailing peak.
Figure 31A:
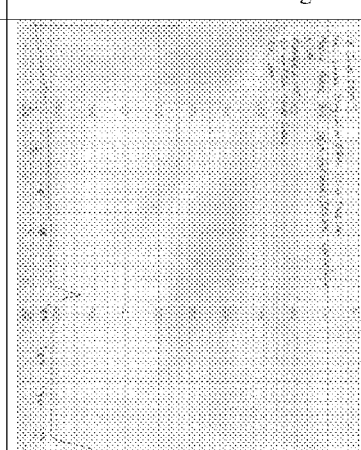
FIG. 31A. The injection and front of the UV trace at 280 nm of a 30 mg load of paclitaxel onto a dried preparative column and eluted with dry 50/50 heptanes/EtOAc. The paclitaxel peak is beginning to elute at the bottom.
Figure 31B:
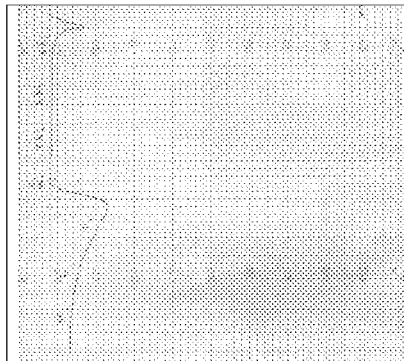
FIG. 31B. The back of the UV trace at 280 nm of a 30 mg load of paclitaxel onto a dried preparative column and eluted with dry 50/50 heptanes/EtOAc.
Figure 32:
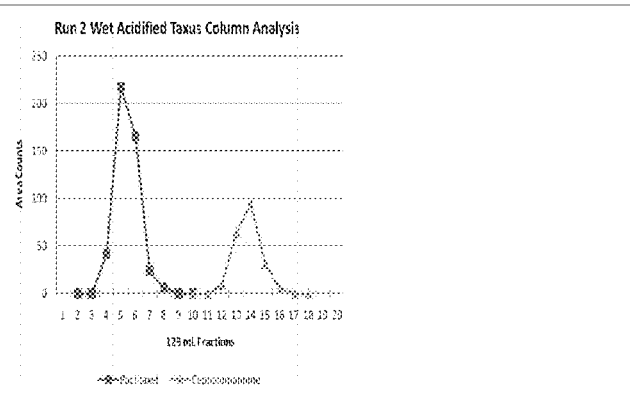
FIG. 32. Column analysis of fractions from Run 2 for paclitaxel and cephalomannine Eluted with wet acidified mobile phase.
Figure 33:
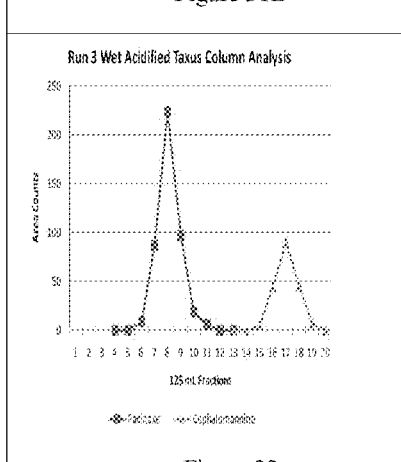
FIG. 33. Column analysis of fractions from Run 3 for paclitaxel and cephalomannine Eluted with wet acidified mobile phase.

The UV traces from Runs 1 and 4 are FIGS. 30 and 31 respectively. The changes in performance of a dried normal phase column observed on an analytical system are also observed on a preparative system. The peak of interest is retained longer, the peak width is greater and the peak tails. Also, when the dried column is re-equilibrated to a hydrated mobile phase, the column performance is restored.

In practice, the isolation and separation of minor constituents from complex mixtures are commonly performed by using a load column and collecting fractions of eluent from the column, analyzing the fractions for the compounds of interest then combining the fractions as appropriate and recovering the materials in these combined fractions for further processing such as another chromatographic operation or crystallization.

Runs 2, 3, 5 and 8 were of the Taxus Extract, 4 grams of extracted material containing approximately 30 mg paclitaxel dried onto DE and loaded from a load column UV traces at 280 nm were collected for these runs however the mixture is too complex and the paclitaxel concentration too small for the UV to register the paclitaxel. Each run was fractionated and the fractions analyzed by HPLC for paclitaxel and cephalomannine.

Runs 2, 3 and 8 were performed on a column equilibrated to the wet acidified mobile phase. Run 5 was performed on the column dried as described above. Table 6 below summarizes the approximate retention times of paclitaxel and cephalomannine in cvs and the peak volumes, the volume of the fractions containing the compound of interest.

FIGS. 32, 33, 34, and 35 are column analyses of Runs 2, 3, 5, and 8 respectively.

TABLE 6

Run number, fraction volume in mLs, paclitaxel retention time in cvs, paclitaxel pool volume in mLs, cephalomannine retention time in cvs, and cephalomannine pool volume in mLs.

| Run # | Fraction Vol, mLs | Pac RT, cvs | Pac Pool, mLs | Ceph RT, cvs | Ceph pool, mLs |
|---|---|---|---|---|---|
| 2 | 125 | 3.4 | 500 | 4.0 | 375 |
| 3 | 125 | 3.6 | 500 | 4.1 | 375 |
| 5 | 1000 | 4.2 | 4000 | 5.2 | 3000 |
| 8 | 125 | 3.6 | 500 | 4.1 | 500 |

Again the compounds of interest are retained longer on the column and the peak widths are broader in normal phase chromatography where the column is dried and the eluant is not intentionally wetted and acidified. Additionally, in this dry system paclitaxel and cephalomannine are not completely separated but overlap in fraction 10. In this practical example of the embodiment of the present application, a normal phase chromatography deliberately executed with a column equilibrated to a hydrated acidified mobile phase performs significantly better than one without hydration and/or acidification. The compounds of interest are well separated and the volumes of solvent in which the compounds of interest are contained ("pools") are relatively small.

Regeneration:

Another aspect of the present application is the methodology for cleaning and re-equilibrating the normal phase column for additional use, regeneration. Regeneration of normal phase columns was performed at analytical scale to show that the regeneration can be accomplished and subsequent column performance is acceptable and reproducible. A description of an embodiment of the application follows which is a typical preparative approach. Run with a wa mobile phase until the compounds of interest have eluted, followed by a more polar regeneration solvent (approximately 1 cv) followed by re-equilibration to the wa mobile phase (approximately 2 cv). The regeneration solvent may or may not contain water as determined by the performance of the subsequent runs. When many repetitive runs of a similar feed are expected to be run there is an opportunity to optimize the regeneration and re-equilibration sequence for water content and regeneration and re-equilibration volumes, possibly reducing the volumes decreasing the solvent necessary and decreasing run times. At preparative scale a way to demonstrate the effectiveness of the regeneration is the measurement of the non-volatile residue washed off the column. Table 7 below shows the quantities of non-volatile residue collected after various runs during the taxus extract demonstration. The values shown are corrected for the non-volatile residue measured in the mobile phase of 0.012 g/liter. The regeneration solution and the first two liters of re-equilibration after the column run, a total of four liters, was evaporated in a rotary evaporator and the residue collected dried in a 45° C. vacuum oven for 15 hours, cooled and weighed. It should be noted that this preparative column had been previously used for other separations with mobile phase compositions ranging from MTBE/methanol/water/acetic acid, quite polar and 6% v/v water, to very non-polar 80/20 heptanes/EtOAc and regenerated as appropriate. Prior to this series of column runs and as part of the equilibration of the column to this mobile phase a regeneration and re-equilibration was performed. This regeneration washed 0.03 grams of residue off the column. The column was used for Run 1, a 30 mg load of paclitaxel standard, and 0.003 gram of residue was collected, indicating the column is quite clean. Runs 2 and 3 are each 4 gram loads of Taxus extract. The regeneration washed 0.49 and 0.73 grams of residue respectively from the column. The regeneration of Run 4, a paclitaxel standard run, was UV clear and not evaluated for residue. The column was dried with 4 cv of dry 95/5 EtOAc/methanol followed by re-equilibration with 2 cv dry 50/50 heptanes/EtOAc. Run 5, a Taxus extract eluted with the dry mobile phase followed by a dry regeneration washed less residue off the column than after the previous Taxus extract runs eluted with the wa mobile phase. The UV trace also suggested that UV adsorbing materials were still eluting from the column at the end of the re-equilibration. Normally, the UV adsorbing materials have been washed off the column before the end of re-equilibration. Between runs 5 and 6 the hydration equilibrium of the column needs to be re-established. The data, UV and non-volatile residue, show that the first regen after run 5 was not as effective as it should be, and that this is due to having dried the column. Therefore, to re-wet or hydrate the column, a second regeneration was performed with 3% v/v water added. This second regeneration washed 0.78 gram of residue off the column The subsequent Runs 6, 7, and 8 with the paclitaxel standard and Taxus extract performed as expected.

TABLE 7

Run number, load type, grams residue recovered from the regeneration of the column and comments.

| Run | load | grams recovered | Comments |
|---|---|---|---|
| na | na | 0.03 | regeneration before this series of runs |
| 1 | standard | 0.003 | |
| 2 | extract | 0.49 | |
| 3 | extract | 0.73 | |
| 5a | extract | 0.25 | after the dry runs |
| 5b | na | 0.78 | regen wetted to re-hydrate the column |
| 7 | standard | 0.20 | |
| 8 | extract | 0.45 | |

Preparative Demonstration with Stevia Glycosides:

The preparative system used for the separation of stevia glycosides is a column nominally 15 cm internal diameter×125 cm length packed with 10 kg Sorbent Technologies catalog number 30930M-25; Silica Gel, 60 Å, 40-63 μm; a Jaeco Fluid Systems duplex pump and a pulse dampener (patent pending), and a nominal 7.5 cm internal diameter×30 cm length load column. Online detection of the stevia glycosides at preparative scale was not possible and therefore eluant fractions were analyzed by a Waters HPLC using a Reverse Phase C18 column and acetonitrile/water gradient at 210 nm.

Figure 36:
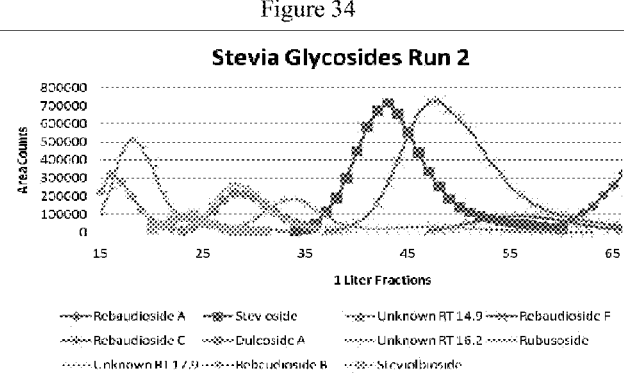
FIG. 36. A Column analysis of a preparative normal phase run of Stevia Extract

The loads of 150 grams of stevia glycosides were dried onto 300-350 grams of diatomaceous earth and packed into the load column. The column operated as described above, load, elute and collect fractions, regenerate, re-equilibrate, load and run the next run. This was performed for 5 runs. The mobile phase, determined by TLC, was 100/18/10/1 EtOAc/methanol/water/acetic acid, 550 mL/minute flow, four each 4 liter forerun fractions and 70 to 75 each one liter fractions collected and analyzed. In the five runs the Rebaudioside C peak apex ranged from fractions 48-50 at about 3.3 cvs. The fractions collected for Rebaudioside C were consistent, nominally fractions 42-61. After each run the column was regenerated with a 50/50 mixture of methanol and mobile phase 0.5 cv followed by 1.5 cv re-equilibration to the mobile phase. The Run 5 regeneration eluant was saved and 24 grams of mass recovered. FIG. 36 is a column analysis of Run 2 which is typical of these runs. Note that this is a 20 liter column packed with irregular 40-63 micron silica gel.

According to the examples detailed above, we have demonstrated that control of the hydration and acidity of the silica phase during normal phase chromatography has unexpected benefits. Additionally an improved design for a continuously compressed bed for column chromatography is disclosed. Finally a technology for cleaning and regeneration of normal phase silica chromatography columns is demonstrated which returns the performance of the column for separations to its original capability. Together these improvements substantially and unexpectedly enhance performance and economics of preparative normal phase chromatography.

What is claimed is:

1. A preparative chromatography column comprising a column tube having a proximal end and a distal end, a proximal distribution assembly comprising an inlet feature on an inlet piston in the proximal end of the column tube, a distal distribution assembly comprising an outlet feature on an outlet piston in the distal end of the column tube, a bed volume between the inlet piston and the outlet piston, wherein the inlet piston is coupled with a thrust washer, a disc spring washer, a disc spring washer guide and a compression cylinder, and wherein the inlet piston is biased against the disc spring for compressing the disc spring washer when the bed volume is filled with a stationary phase.

2. The preparative chromatographic column of claim 1, wherein the compression cylinder is coupled to a plurality of disc spring washers.

3. The preparative chromatographic column of claim 1, wherein the inlet piston is coupled with a plurality of thrust washers.

4. The preparative chromatographic column of any one of claim 1, wherein the plurality of disc spring washers are stacked in series and/or in parallel.

5. The preparative chromatographic column of claim 1, further comprising internal threading and threaded nuts for coupling of the proximal distribution assembly with the distal distribution assembly with the column tube.

6. The preparative chromatography column of claim 1, wherein the thrust washer and disc spring washer provides axial compression and/or maintains compression on the bed volume comprising chromatographic packing material.

* * * * *